US012083028B2

(12) United States Patent
Lindhe et al.

(10) Patent No.: US 12,083,028 B2
(45) Date of Patent: Sep. 10, 2024

(54) QUICK COUPLING

(71) Applicant: C LindheXtend AB, Halmstad (SE)

(72) Inventors: Christoffer Lindhe, Halmstad (SE); Patrik Svensson, Halmstad (SE)

(73) Assignee: C LindheXtend AB, Halmstad (SE)

( * ) Notice: Subject to any disclaimer, the term of this patent is extended or adjusted under 35 U.S.C. 154(b) by 493 days.

(21) Appl. No.: 16/627,853

(22) PCT Filed: Jul. 13, 2018

(86) PCT No.: PCT/EP2018/069181
§ 371 (c)(1),
(2) Date: Dec. 31, 2019

(87) PCT Pub. No.: WO2019/012152
PCT Pub. Date: Jan. 17, 2019

(65) Prior Publication Data
US 2020/0121477 A1  Apr. 23, 2020

(30) Foreign Application Priority Data
Jul. 14, 2017  (SE) .................................... 1750931-6

(51) Int. Cl.
*A61F 2/78* (2006.01)
*A61F 2/50* (2006.01)
(Continued)

(52) U.S. Cl.
CPC .................. *A61F 2/50* (2013.01); *A61F 2/54* (2013.01); *A61F 2/60* (2013.01); *A61F 2/80* (2013.01);
(Continued)

(58) Field of Classification Search
CPC ............................................... A61F 2002/6854
See application file for complete search history.

(56) References Cited

U.S. PATENT DOCUMENTS

| 3,659,294 A | 5/1972 | Glabiszewski |
| 4,564,365 A | 1/1986 | Winner et al. |
| (Continued) | | |

FOREIGN PATENT DOCUMENTS

| EP | 0267347 A1 | 5/1988 |
| JP | 2003250823 A | 9/2003 |
| WO | 9827374 A1 | 6/1998 |

OTHER PUBLICATIONS

International Search Report for corresponding International Application No. PCT/EP2018/069181 dated Dec. 11, 2018.
(Continued)

*Primary Examiner* — Jacqueline Woznicki
(74) *Attorney, Agent, or Firm* — Renner, Otto, Boisselle & Sklar, LLP

(57) ABSTRACT

A prosthetic coupling device including a first coupling part and a second coupling part is provided. The first coupling part has a first end and a second end and the second coupling part has a first end and a second end. The first end of the first coupling part is connectable to the first end of the second coupling part, and the second end of the first coupling part is connectable to a prosthetic adapter element of a first prosthetic member. The second end of the second coupling part is connectable to a prosthetic adapter element a second prosthetic member. The prosthetic coupling device further includes first and second manually operable locking arrangements, which are separately operable and each locking arrangement has a locked configuration and a release configuration. Furthermore, the prosthetic coupling device is transferable from a connected state to a disconnected state only when both of the locking arrangements are in the release configuration. A use of a prosthetic coupling device is also provided. Further, a prosthetic assembly is also provided. A coupling part for use in the coupling device is (Continued)

also provided. method for connecting and disconnecting a first prosthetic member to a second prosthetic member is also provided.

15 Claims, 14 Drawing Sheets

(51) Int. Cl.
*A61F 2/54* (2006.01)
*A61F 2/60* (2006.01)
*A61F 2/80* (2006.01)
*A61F 2/68* (2006.01)

(52) U.S. Cl.
CPC .......... *A61F 2002/5083* (2013.01); *A61F 2002/6854* (2013.01); *A61F 2/78* (2013.01); *A61F 2002/7887* (2013.01)

(56) References Cited

U.S. PATENT DOCUMENTS

| | | | |
|---|---|---|---|
| 4,938,775 A * | 7/1990 | Morgan | A61F 2/60 623/27 |
| 5,435,604 A | 7/1995 | Chen | |
| 5,961,245 A * | 10/1999 | Garin | B62D 1/16 280/779 |
| 6,224,113 B1 | 5/2001 | Chien | |
| 9,696,884 B2 | 7/2017 | Morgan et al. | |
| 2005/0049720 A1 | 3/2005 | Benson | |
| 2006/0079965 A1 | 4/2006 | Benson | |
| 2012/0245707 A1 | 9/2012 | Osgyan et al. | |
| 2015/0377397 A1 | 12/2015 | Aquistapace et al. | |

OTHER PUBLICATIONS

Written Opinion of the International Searching Authority for corresponding International Application No. PCT/EP2018/069181 dated Dec. 11, 2018.

* cited by examiner

QUICK COUPLING

This application is a national phase of International Application No. PCT/EP2018/069181 filed Jul. 13, 2018 and published in the English language, which claims priority to Swedish Application No. 1750931-6 filed Jul. 14, 2017, both of which are hereby incorporated herein by reference.

TECHNICAL FIELD

The present invention relates to a prosthetic coupling device for detachably connecting two prosthetic components together, and more particularly it relates to a quick coupling for prostheses that is safe to use and which may be handled without tools. The invention also relates to a method for connecting and disconnecting two prosthetic members.

BACKGROUND

Artificial limbs, or prostheses, have been used by amputees for many centuries. From their beginnings, they have evolved from crudely shaped sticks, pegs or hooks, into sophisticated electro-mechanical equipment, occasionally incorporating servomotors and micro-processors to produce more natural limb movement. However, even given such development, problems remain in the means for attaching and detaching a prosthetic member to the amputation site.

Problems associated with the changing of the prosthesis have increased as amputees have acquired more than one prosthesis for use in differing situations and environments. Therefore, the course of development of prostheses has dictated a need for more effective means for rapidly changing from a prosthesis intended for one purpose to another prosthesis intended for use in another purpose or application.

In situations wherein the prosthesis is frequently removed it is essential that the release mechanism is durable, self-aligning, safe and does not require the use of tools that have to be carried by the user or assistance from an assistant or orthotic fitter. Furthermore, it is desirable that any user-specific adjustments and settings made to the prosthesis remain unaffected when removing the prosthesis such that the prosthesis can be reattached with all user-specific settings intact.

Lower-extremity prostheses provide replacements at varying levels of amputation. These include hip disarticulation, transfemoral prosthesis, knee disarticulation, trans-tibial prosthesis, Syme's amputation, foot, partial foot, and toe. The two main subcategories of lower extremity prosthetic devices are trans-tibial (any amputation transecting the tibia bone or a congenital anomaly resulting in a tibial deficiency) and trans-femoral (any amputation transecting the femur bone or a congenital anomaly resulting in a femoral deficiency).

A typical prosthetic leg structure for above the knee amputee consists of a socket which is the part that comes in direct contact with the amputee's residual limb (unless the user is fitted with an osseointegration (also called an osseointegrated coupling); a pylon which is the portion of the prosthesis that transfers weight between the socket and the prosthetic knee, a knee, and a foot with a pylon to transfer weight between the foot and the knee.

A number of mechanisms have been designed to connect and release the lower-extremity prosthetic components to a prosthetic socket or a direct bone attachment (osseointegration) of the user.

US 2005/049720 A1 discloses a quick-release tube clamp for locking and releasing a prosthetic pylon/foot component from the socket without the use of a special tool. The quick-release mechanism does not require any alignment in the seating of the locking mechanism, does not rotate when in the locking position, and does not require modification of conventional pylon/foot components. The clamp portion firmly locks a tubular portion around a tubular pylon when the tubular pylon is inserted into the tubular position and provides a releasing position for removal of the tubular pylon. However, if the quick-release tube clamp accidently becomes undone, the prosthetic foot will be disconnected from the socket, which may cause the amputee to fall. Furthermore, even if the quick coupling of US 2005/049720 A1 provides for an easy way of locking and releasing a prosthetic pylon/foot component from the socket without the use of a special tool, it does not ensure that the prosthetic foot is fitted in an incorrect way.

A further example of a known quick-release mechanism for a limb prosthesis is disclosed in U.S. Pat. No. 4,564,365A.

SUMMARY

An object of the present teachings is to eliminate or at least mitigate the drawbacks of prior-art systems. This object has now been achieved, in full or at least in part, by the novel technique set forth in the appended independent claims; preferred embodiments being defined in the dependent claims.

In a first aspect of the present teachings there is provided a coupling for use in the connection and disconnection of one prosthetic element to a socket portion, alternatively to an osseointegration, of an amputation site or a further prosthetic element.

Particularly, there is provided a prosthetic coupling device comprising a first coupling part and a second coupling part, the first coupling part comprising a first end and a second end and the second coupling part comprising a first end and a second end. The first end of the first coupling part being connectable to the first end of the second coupling part, the second end of the first coupling part being connectable to a prosthetic adapter element of a first prosthetic member, and the second end of the second coupling part being connectable to a prosthetic adapter element on a second prosthetic member. The prosthetic coupling device further comprises first and second manually operable locking arrangements being separately operable and each locking arrangement having a locked configuration and a release configuration, the coupling device being transferable from a connected state to a disconnected state only when both of the locking arrangements are in the release configuration.

The prosthetic coupling devices described herein are primarily configured for use with trans-femoral and trans-tibial prostheses for below-the-knee or above-the-knee amputees. For example the prosthetic coupling devices may be used to connect a first prosthetic member such as a prosthetic foot to a second prosthetic member such as a lower end of a lower leg or alternatively the coupling device may be used to connect a knee joint to a lower end of an upper leg. The prosthetic coupling device may also be used for connecting prosthetic members to other limbs such as e.g. arms.

The prosthetic coupling devices described herein comprise a first coupling part and a second coupling part that can be connected or disconnected from each other. Each first and second coupling part comprises a first and a second end. The first ends of said first and second coupling parts are configured to be connectable to each other in a mutually fitting configuration such that when both locking arrangements are in operation, the prosthetic coupling device forms a tight, safe and stable link between two prosthetic members.

The second ends of each first and second coupling parts are being connectable to a prosthetic adaptor element of a first and second prosthetic member respectively. Prosthetic adapters are adjustable links designed to interconnect adjoining prosthetic members of a prosthetic limb. A prosthetic adapter element (also called a prosthetic adapter link) typically includes a male and a female adapter element respectively. Said male and female adapter elements are arranged on two artificial prosthetic limb members to be interconnected, one on each limb member. The male adapter element, which may be arranged on a first prosthetic member, may e.g. have a spherically convex base from which a substantially frustopyramidal boss rises divergingly, and, in this case, the female adapter element, arranged on the second prosthetic member, comprises an annular socket configured to receive the frustopyramidal boss. To connect the two prosthetic elements, the male adapter element is inserted into the female adapter element. For example, a prosthetic adapter can be used to interconnect a stump support and a thigh member, a knee joint and a member forming a lower leg or at the ankle for connecting the lower end of a lower leg member and an artificial foot.

Prosthetic adapters are well known to the person skilled in the art of orthotics. Thus, according to one embodiment of the present teachings, the prosthetic adaptor elements of said first or second prosthetic members are selected from the group consisting of 4-hole adapter, male pyramid adapter, female pyramid adapter, and pylon adapter of different variants. Thus, according to one embodiment, the prosthetic adaptor elements of said first or second prosthetic members are selected from the group consisting of 4-hole Linking plates, 4-hole male pyramids, 4-hole female pyramids, 4-hole pyramid receiver adapters, female double adapters, male double adapters, male-female double adapters, Sach foot adapters, female pylons, male adapters, female adapters, male tube clamps, female tube clamps, and/or 4-hole tube clamps.

As the skilled person realizes that the types of adapter connections at the second ends depend on the kind of prosthetic elements to be interconnected by the coupling device. The adaptor connections at the second ends of the first and second coupling parts may thus be the same or different. Some specific examples are a 4-hole male pyramid and a 4 hole female pyramid; 4-hole adapter, male pyramid adapter, female pyramid adapter, and pylon adapter of different variants.)

The pylon adapter may have a circular cross section and have a diameter between 22 and 35 mm, such as e.g. 22 mm or 30 mm.

The pylon adapter may have a rectangular cross section.

One adapter widely used for connecting prosthetic members is a pyramid adaptor. One such pyramid adapter is described in U.S. Pat. No. 3,659,294A.

The prosthetic adapter of the first prosthetic members may a male pyramid adapter. In such a case, the second end of the first coupling part is a female pyramid adapter.

The prosthetic adapter of the first prosthetic members may a female pyramid adapter. In such a case, the second end of the first coupling part is a male pyramid adapter.

The prosthetic adapter of the second prosthetic members may a male pyramid adapter. In such a case, the second end of the second coupling part is a female pyramid adapter.

The prosthetic adapter of the second prosthetic members may a female pyramid adapter. In such a case, the second end of the second coupling part is a male pyramid adapter.

The body structure of the user and his or her attitude when standing or walking may require certain adjustments in the relative position of various components in the artificial leg. Frequently, these adjustments must be made in two mutually orthogonal planes: in the anterior-posterior plane and in the lateral-medial plane. Thus, the contact surfaces on the male adapter element of a prosthetic component comprise the respective sides of the preferably four-sided frustopyramid. Set-screws bearing upon these sides extend at right angles and are lodged in the socket for engaging the contact surfaces of the boss for retaining the prosthetic component in a selected angular position. This user-specific alignment has to be performed by a professional prosthetist and once aligned it should not be interfered with. It has heretofore not been possible to change between different prostheses, such as prostheses specially adapted for different activities, without having to provide each prosthesis with a prosthetic adaptor adjusted to the settings required by the user. By means of the prosthetic coupling device as disclosed herein, it is possible to use the same prosthetic adaptor element which has been adjusted by a professional prosthetist for attaching different prostheses.

Accordingly, a major advantage with the prosthetic coupling device as described herein is that there is no need to interfere with this crucial alignment as each of the first and second coupling parts are connectable to prosthetic adapter elements present on the first and second prosthetic members to be interconnected. For example, if the prosthetic coupling device as described herein is to interconnect a prosthetic foot comprising a male adapter element to the lower end of a lower leg member, the first coupling part of the prosthetic coupling device advantageously comprises a female adapter element, i.e. a socket, that is connectable to the male adapter element of the prosthetic foot. The female adapter element, i.e. in this case a socket, which comprises the four set-screws that bear upon four-sided frustopyramid of the male adapter element, is aligned as required to fit the user. The second coupling part of the prosthetic coupling device is connectable to the lower end of the lower leg member. In this case, the second coupling part of the prosthetic coupling device may be a female tube clamp.

Advantageously, the user has a set of several prosthetic feet suitable for different conditions that are all fitted with a first coupling part having a second end (i.e. a female socket with four set screws) that have been aligned by a professional prosthetist. In this way the user may easily change feet depending on the situation at hand.

In case the second end of the first coupling part is to be connected to a tube element of a prosthetic member, the tube clamp may fit a tubular element having a standard tube diameter such as 30 mm or 34 mm.

In case the second end of the second coupling part is to be connected to a tube element of a prosthetic member, the tube clamp may fit a tubular element having a standard tube diameter such as 30 mm or 34 mm. Generally, for adult amputees, the tube diameter is 30 mm. For children or adolescents, the tube diameter will generally be less than 30 mm, typically 20 mm.

The prosthetic coupling device comprises first and second manually operable locking arrangements being separately operable and each having a locked configuration and a release configuration The first and second locking arrangements are arranged to lock the first and second coupling parts together in a locked configuration when the prosthetic coupling device is in a connected state, and to be released to bring the prosthetic coupling device into a disconnected state. In the connected state the prosthetic coupling device is firmly locked such that there is no play (i.e. mobility) between the first and second coupling parts. In the disconnected state the first and second coupling parts have become completely separated and prosthetic members may be interchanged.

The first and second locking arrangements are operable separately from each other such that the first and second locking arrangements are two different locking arrangements which are operable independently of each other. This means that if the user wants to change the prosthetic coupling device from a connected state to a disconnected state he or she must first release the second locking arrangement from its locked configuration and thereafter release also the first locking arrangement from its locked configuration. If the user wants to change the prosthetic coupling device from a disconnected state to a connected state he or she must first transfer the first locking arrangement into a locked configuration and thereafter, in a separate step, transfer also the second locking arrangement into a locked configuration.

According to one embodiment, the first and second locking arrangements are independently selected from slide-in couplings, clamp couplings, spring bolt couplings, snap-fit couplings, and/or rotatable couplings. The first and second locking arrangements are preferably of different types. This means that they are not both e.g. snap-fit couplings. The first and second locking arrangements may be the same or different.

Thus, according to another embodiment, the first and second locking arrangements are of different types. Thus, the prosthetic coupling device may e.g. have a first locking arrangement that is of a slide-in coupling type and a second locking arrangement that is a snap-fit coupling.

Examples of slide-in couplings are for example hinged connections as described below wherein a pin provided on one coupling part is configured to be inserted into a knuckle provided on a second coupling part, thereby connecting the coupling parts such that an axial movement is created between the first and second coupling parts along the axle of the pin.

A further example of a slide-in coupling may be one or more grooves mating with one or more ridges wherein the groove(s) and ridge(s) are provided on the first and second coupling parts.

A spring bolt coupling type locking mechanism comprises a spring-loaded bolt with an angled edge. When the first and second coupling devices are brought together, the angled edge of the latch bolt engages with a lip or a strike surface on the second coupling part and the bolt itself will retract due to the pressure of contact with the lip or strike surface; once the bolt passes a certain point, it will fully extend and quickly lock into an aperture in the lip or strike plate due to the pressure being released from the spring. The fully extended bolt will hold the two coupling parts together. The latch bolt is disengaged (retracted) from the aperture typically when the user manually retracts the latch bolt, allowing the two coupling parts to separate. The spring loaded push-button described herein is an example of a spring bolt coupling.

A clamp coupling joins two shafts and is either two-piece or split and compresses the coupling around the shaft.

A snap-fit coupling is an assembly method used to attach flexible parts, usually plastic, to form the final product by pushing the parts' interlocking components together. There are a number of variations in snap fits, including cantilever, torsional and annular. Most snap-fit joints have a common design of a protruding edge and a snap-in area. A cantilever snap-fit usually has a lever or pin to be pushed, in order to undo the snap-fit design.

A rotatable coupling is a type of coupling that connects two parts using interlocking hooks and flanges. Two opposing couplings are pressed together such that the hooks of each one are inserted into the slots in the flange of the other. Then they are rotated in opposite directions until they are tight, or latches engage. To uncouple them, the latches are released and the connectors are turned in the opposite directions from coupling, and then separated when the hooks and slots are aligned.

Another example of a rotatable coupling is the bayonet mount consisting of a cylindrical male side with one or more radial pins, and a female receptor with matching L-shaped slot(s) and with spring(s) to keep the two parts locked together. The slots are shaped like a capital letter L with serif (a short upward segment at the end of the horizontal arm); the pin slides into the vertical arm of the L, rotates across the horizontal arm, then is pushed slightly upwards into the short vertical "serif" by the spring; the connector is no longer free to rotate unless pushed down against the spring until the pin is out of the "serif".

The first and second locking arrangements are manually operable which means that no tools are required to transfer the prosthetic coupling device from a connected state to a disconnected state. Nor is a tool required to transfer the prosthetic coupling device from a disconnected state to a connected state. Both the first and second locking arrangements can easily be handled by the user without the use of tools or the help from a professional prosthetist. Advantageously the first and second locking arrangements can be handled by using only one hand.

According to another embodiment, said first locking device is a spring loaded push-button. Such a spring loaded push-button may also be referred to a spring bolt coupling type locking mechanism as described above.

According to another embodiment, said second locking device is a screw having a shaft with a conical end. The conical end may also be referred to as a conical wedge. The wedge is spring loaded. The shaft has a thread that can be tightened. When tightening the thread the conical wedge will be pressed in to a through-hole in the first and second coupling parts and force the two parts towards each other and secure the locking.

According to another embodiment said first locking device is a spring loaded push-button and said second locking device is a screw having a shaft with a conical end.

According to yet another embodiment, an intermediate locking state of the prosthetic coupling device is assumed between the connected state and the disconnected state. The coupling device as disclosed herein is transferable from the connected state to the disconnected state only when both the locking arrangements are in the release configuration. For safety reasons, both the first and second locking arrangements have to be released before the prosthetic coupling device can be transferred into the disconnected state. If only one of the first or second locking arrangements has been released by the user, or if it has been released by accident, the first and second coupling parts will not disconnect completely. Instead, the coupling device will assume an intermediate locking state in which a small amount of play or mobility will appear between the two coupling parts, which will make the user aware of an instability in the coupling device indicating that something has happened to the prosthetic coupling device and thereby take appropriate measures.

Hence, according to another embodiment, there is a mobility between said first and second coupling parts when said prosthetic coupling device has assumed an intermediate locking state.

According to another embodiment, said locking arrangements of said first ends of the first and second coupling parts comprise mating guide members. In other words, said first ends of said first and second coupling parts comprise mating guide members. The mating guide members guarantee that the first and second prosthetic members are properly connected to one another. The first and second coupling parts are fitted with a first and second mating guide member respectively. The first and second mating guide members will permit connection of the two coupling parts only if the first and second coupling parts are properly aligned. If the coupling parts are not properly aligned, the two mating guide members will not allow coupling of the prosthetic coupling device. In other words, the mating guides can only fit together in one way, i.e. when the two coupling parts only if the first and second coupling parts are properly aligned.

The mating guide members may comprise a protrusion on one coupling part and a three-dimensional complementary recess on the other coupling part. The protrusion and the recess fit together in only one way, such as a key in a lock.

The mating guide members may comprise one or more protrusions on one coupling part and three-dimensional complementary recesses on the other coupling part. Preferably, the protrusion is on the first end of the first coupling part, and the recess is located on the first end of the second coupling part The mating guide members may comprise one or more protrusions and one or more recesses on one coupling part and three-dimensional complementary recesses and protrusions on the other coupling part.

Examples of such mating guide members is a protrusion and corresponding recess formed as a trapezium, an irregular quadrilateral, an isosceles triangle, or a scalene.

One preferred example of such mating guide members is a protrusion formed as a trapezium on one of the coupling parts and a recess formed as a complementary trapezium on the other coupling part. Preferably, the protrusion formed as a trapezium is on the first end of the first coupling part, and the recess formed as a trapezium is located on the first end of the second coupling part.

In a second aspect of the present teachings there is provided a use of a coupling device according to the present teachings.

In a third aspect of the present teachings there is provided a prosthetic assembly configured to be attached to a prosthetic socket or to an osseointegrated coupling, wherein the assembly comprises two prosthetic members interconnected by a coupling device according to the present teachings.

In a fourth aspect of the present teachings there is provided a coupling part for use in a coupling device according to the present teachings.

The present teachings also provides a first coupling part for use in a coupling device according to the present teachings. The first coupling part comprises a first end and a second end and said first end of the first coupling part is connectable to a first end of a second coupling part of the coupling device. Further, said second end of the first coupling part is connectable to a prosthetic adapter element of a prosthetic member.

The present teachings also provides a second coupling part for use in a coupling device according to the present teachings. The second coupling part comprises a first end and a second end and said first end of the second coupling part is connectable to a first end of a first coupling part of the coupling device. Further, said second end of the second coupling part is connectable to a prosthetic adapter element on a prosthetic member.

In a fifth aspect of the present teachings there is provided a method for connecting and disconnecting a first a prosthetic member to a second prosthetic member, wherein a first locking arrangement of the prosthetic coupling device according to the present teachings, is transferred from a release configuration to a locked configuration, whereby said prosthetic coupling device assumes an intermediate locking state; and wherein a second locking arrangement of the prosthetic coupling device is transferred from a release configuration to a locked configuration, whereby said prosthetic coupling device is transferred from a disconnected state to a connected state; and wherein thereafter said second locking arrangement is transferred from a locked configuration to a release configuration, whereby said prosthetic coupling device assumes an intermediate locking state; and wherein said first locking arrangement is transferred from a locked configuration to a release configuration, whereby said prosthetic coupling device is transferred from a connected state to a disconnected state.

To connect a first a prosthetic member to a second prosthetic member, a first locking arrangement of the prosthetic coupling device is transferred from a release configuration to a locked configuration, whereby said prosthetic coupling device assumes an intermediate locking state. Thereafter a second locking arrangement of the prosthetic coupling device is transferred from a release configuration to a locked configuration, whereby said prosthetic coupling device has been transferred from a disconnected state to a connected state.

Thus, in a sixth aspect of the present teachings there is provided a method for connecting a first a prosthetic member to a second prosthetic member, wherein a first locking arrangement of the prosthetic coupling device according to the present teachings, is transferred from a release configuration to a locked configuration, whereby said prosthetic coupling device assumes an intermediate locking state; and wherein a second locking arrangement of the prosthetic coupling device is transferred from a release configuration to a locked configuration, whereby said prosthetic coupling device is transferred from a disconnected state to a connected state.

To disconnect a seventh a prosthetic member from a second prosthetic member said second locking arrangement is transferred from a locked configuration to a release configuration, whereby said prosthetic coupling device assumes an intermediate locking state. Thereafter, said first locking arrangement is transferred from a locked configuration to a release configuration, whereby said prosthetic coupling device is transferred from a connected state to a disconnected state.

Thus, in a eighth aspect of the present teachings there is provided a method for disconnecting a first a prosthetic member from a second prosthetic member, wherein a second locking arrangement of the prosthetic coupling device according to the present teachings is transferred from a locked configuration to a release configuration, whereby said prosthetic coupling device assumes an intermediate locking state; and wherein said first locking arrangement is transferred from a locked configuration to a release configuration, whereby said prosthetic coupling device is transferred from a connected state to a disconnected state.

DETAILED DESCRIPTION

Figure 1:
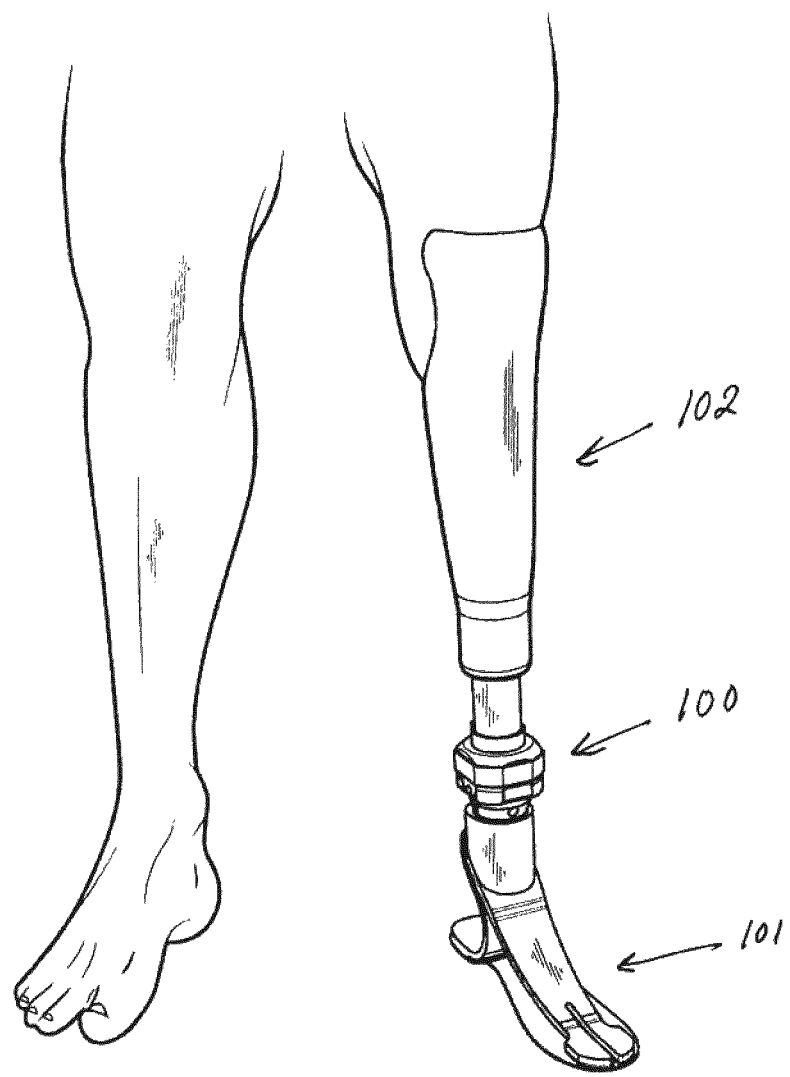
FIG. 1 discloses a prosthetic limb comprising a first prosthetic member and a second prosthetic member interconnected by a prosthetic coupling device.

In the following, the prosthetic quick coupling will be described in a non-limiting way and in more detail with reference to exemplary embodiments illustrated in the enclosed drawings, in which the first digit of the reference numerals refers to the figure in which the element is shown, while the two subsequent digits denotes the particular element. It is to be understood that other embodiments are contemplated and may be made without departing from the scope or spirit of the present teachings. The following detailed description, therefore, is not to be taken in a limiting sense.

The prosthetic coupling devices described herein are configured for use with trans-femoral and trans-tibial prostheses for above-the-knee or below-the-knee amputees, respectively. The same concepts and methods described may be similarly used for other prosthetic devices and are not limited solely to the anatomical locations discussed.

FIG. 1 discloses a prosthetic limb comprising a first prosthetic member 101 and a second prosthetic member 102 interconnected by a prosthetic coupling device 100. In this embodiment, the prosthetic coupling device 100 interconnects a prosthetic foot with a lower end of a lower leg. However, the prosthetic coupling device may also connect e.g. a knee joint to a lower end of an upper leg.

Figure 2:
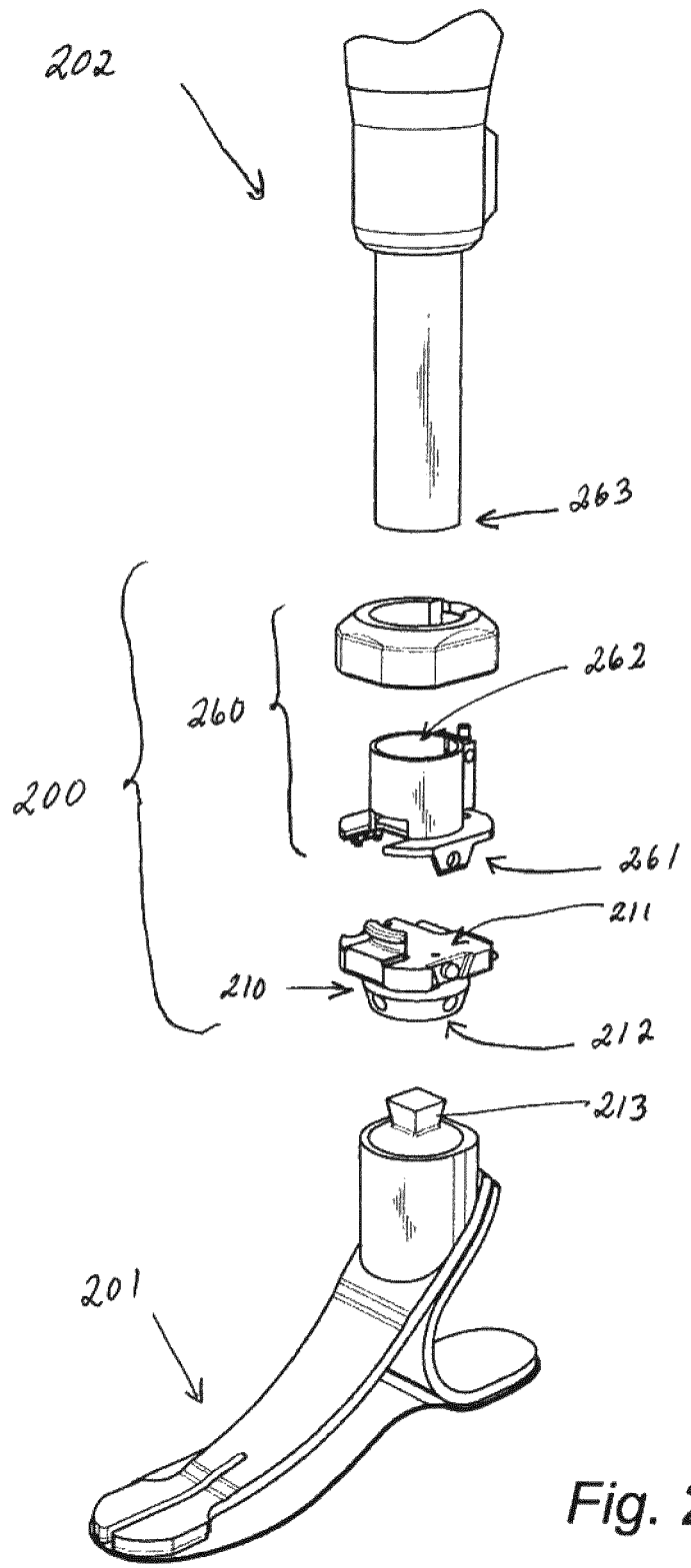
FIG. 2 discloses an exploded view of one embodiment of a prosthetic coupling device.

FIG. 2 discloses one embodiment of a prosthetic coupling device 200 as described herein. The prosthetic coupling device comprises a first coupling part 210 and a second coupling part 260. The second end 212 of the first coupling part 210 is connectable to a first prosthetic adapter element 213, which in this embodiment is a male adapter element provided on a prosthetic foot. Thus, the second end 212 of the first coupling part 210 is in this embodiment fitted with an annular socket portion with four set-screws disposed therearound which are used to connect to a pyramidal boss of a male adapter element (i.e. the prosthetic adapter element 213 of the first prosthetic member 201 (in this case a prosthetic foot)) in a conventional manner. The second end 262 of the second coupling part 260 is connectable to a prosthetic adapter element 263 on a second prosthetic member 202 (which in this case is a lower end of a lower leg). In this embodiment, the second end 262 of the second coupling part 260 contains a female tube clamp. The first coupling part 210 has a first end 211 which is connectable to a first end 261 of the second coupling part 260 in a mating configuration.

Figure 3A:
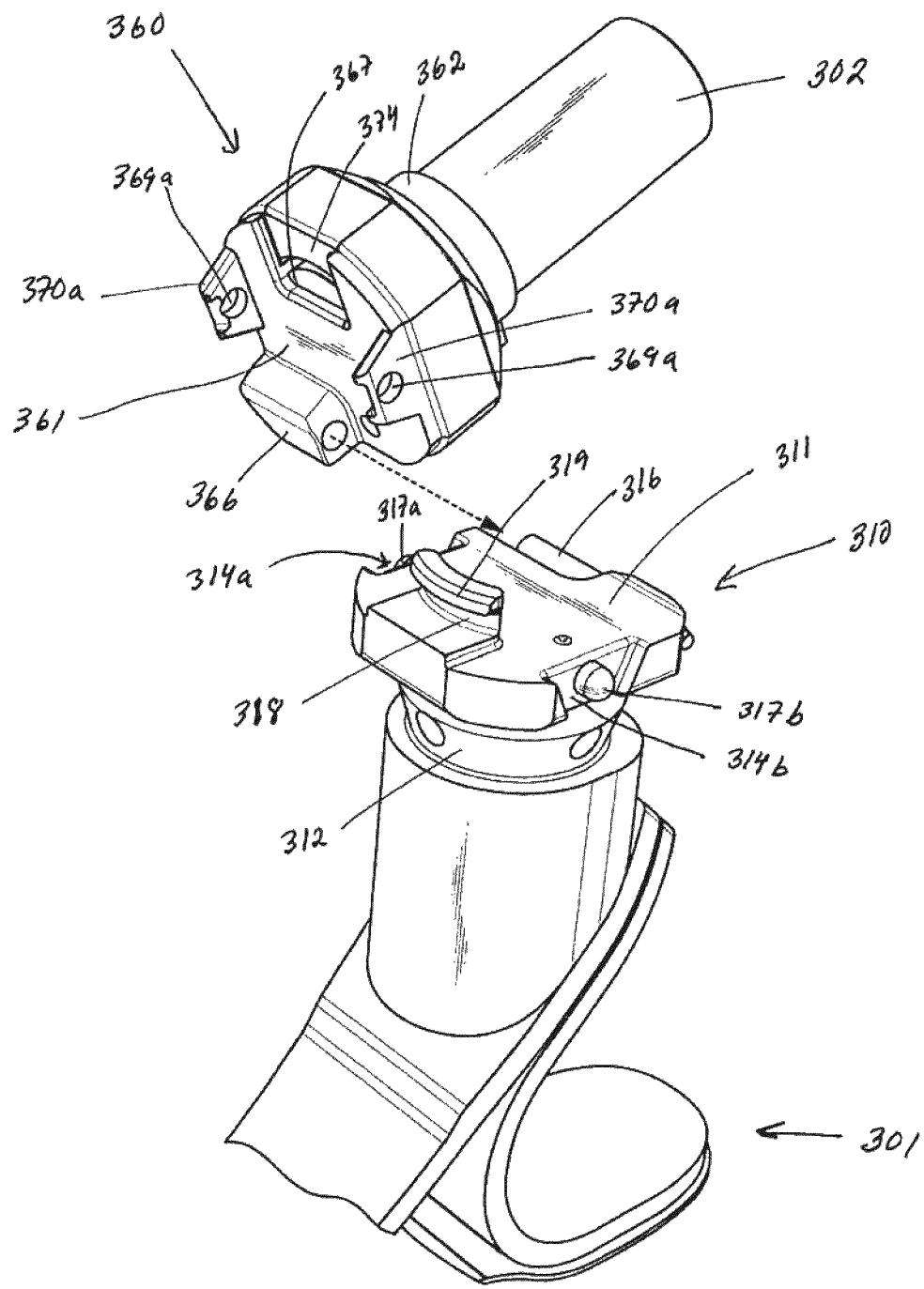
FIGS. 3a-d disclose a more detailed view of the prosthetic coupling device shown in FIGS. 1 and 2.

FIGS. 3a-d disclose a more detailed view of the prosthetic coupling device shown in FIGS. 1 and 2. In FIG. 3a it is seen that, in this embodiment, the first and second coupling parts 310, 360 each have first ends 311, 361 comprising surfaces that will fit together in a mating configuration and which are connectable to one another by means of a hinged connection and a spring loaded push-button. The first end 311 of the first coupling part comprises a pin 316 configured to fit into a first locking arrangement 366, in this case a knuckle, creating a joint of a hinge connecting the first ends 311, 361 of the first and second coupling parts 310, 360.

The first end 311 (i.e. the mating surface) of the first coupling part 310 further also comprises a first locking arrangement 318, in this case a locking protrusion configured to fit into an aperture 367 arranged in the first end 361 (i.e. the mating surface) of the second coupling part 360. Spring loaded push-buttons 317a,b, forming a first locking arrangement 317, are arranged on opposing peripheral side walls 314a,b of the first coupling part 310 and are configured to spring into through-holes 369a,b provided in lips 370a,b which are arranged at the peripheral edges of the first end 361 (i.e. the mating surface) on the second coupling part 360. The hinged connection, i.e. the pin 316 and the knuckle (first locking arrangement 366), together with the spring loaded push-buttons 317a,b form a first locking arrangement.

Figure 3B:
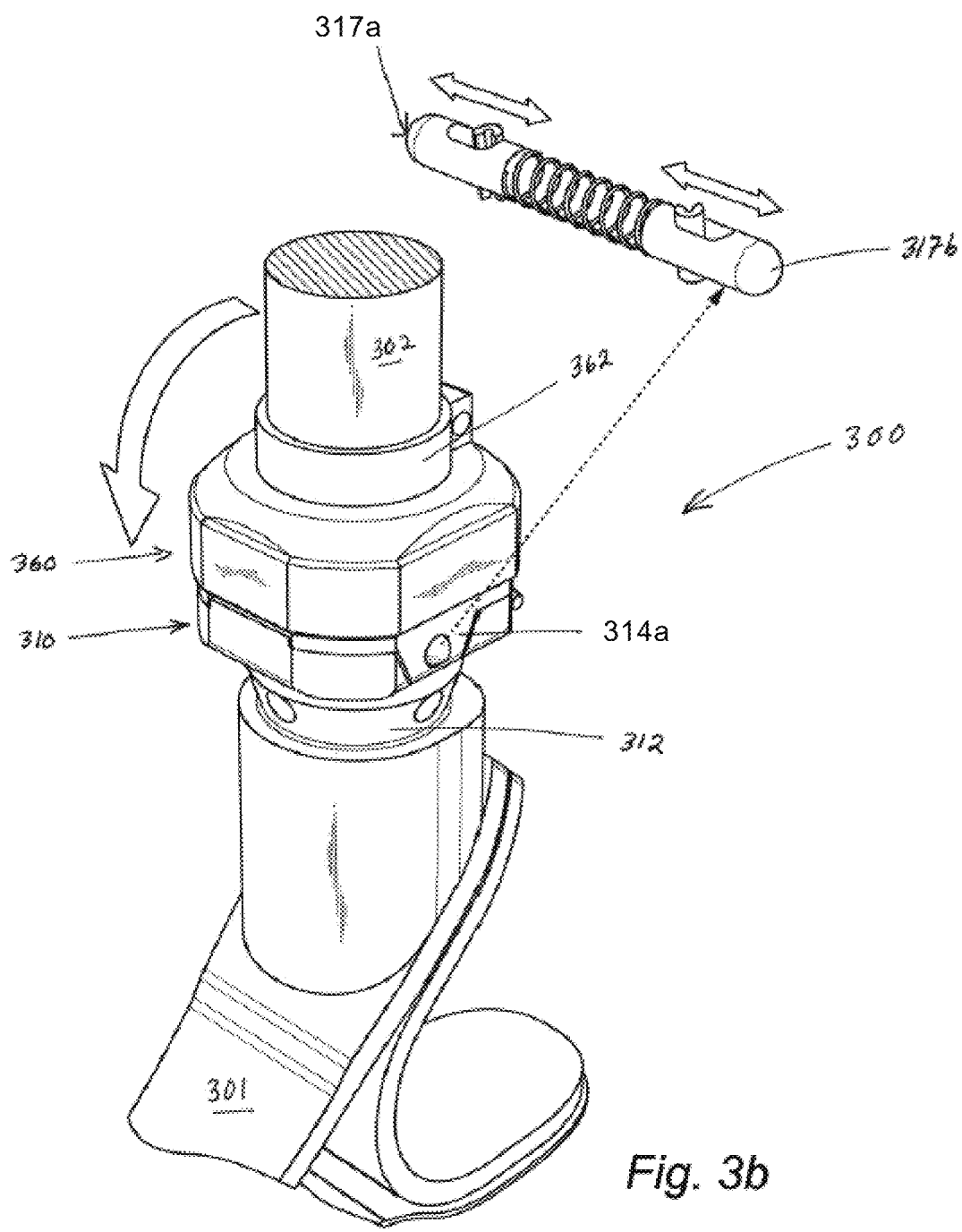

The first locking arrangement is transferred into a locked configuration by first sliding the pin 316 of the first coupling part 310 into the knuckle of the second coupling part 360 thereby connecting the first and second coupling parts 310, 360 such that an axial movement is created between the first and second coupling parts 310, 360 along the axle of the pin 316 (see arrow in FIG. 3b).

The two mating surfaces, i.e. the first end 311 of the first coupling part 310 and the first end 361 of the second coupling part 360 are thereafter pressed together such that the locking protrusion, i.e. the first locking arrangement 318, enters the aperture 367 located in the mating surface, i.e. the first end 361 of the second coupling part 360, while the two spring loaded push-buttons 317a,b are pushed into the peripheral side walls 314a,b of the first coupling part 310 by the lips 370a,b of the second coupling part 360. The lower edges of the lips 370a,b are chamfered, which facilitates the pushing of the spring loaded push-buttons 317a,b into the through-holes 369a,b. The spring loaded push-buttons 317a,b will not spring back until they align with the through-holes 369a,b on the lips 370a,b of the second coupling part 360. The first locking arrangement of the prosthetic coupling device has thereby been transferred into a locked configuration.

Although the two coupling parts 310, 360 are securely connected to one another and will not come apart unless the spring loaded push-buttons 317a,b are pressed towards the peripheral walls 314a,b such that they exit the through-holes 369a,b on the lips 370a,b, there is still a small amount of mobility existing between the two coupling parts 310, 360. The mobility indicates that the prosthetic coupling device 300 is in an intermediate locking state and that the second locking arrangement has not yet been transferred into the locked configuration.

Figures 3C, 3D:
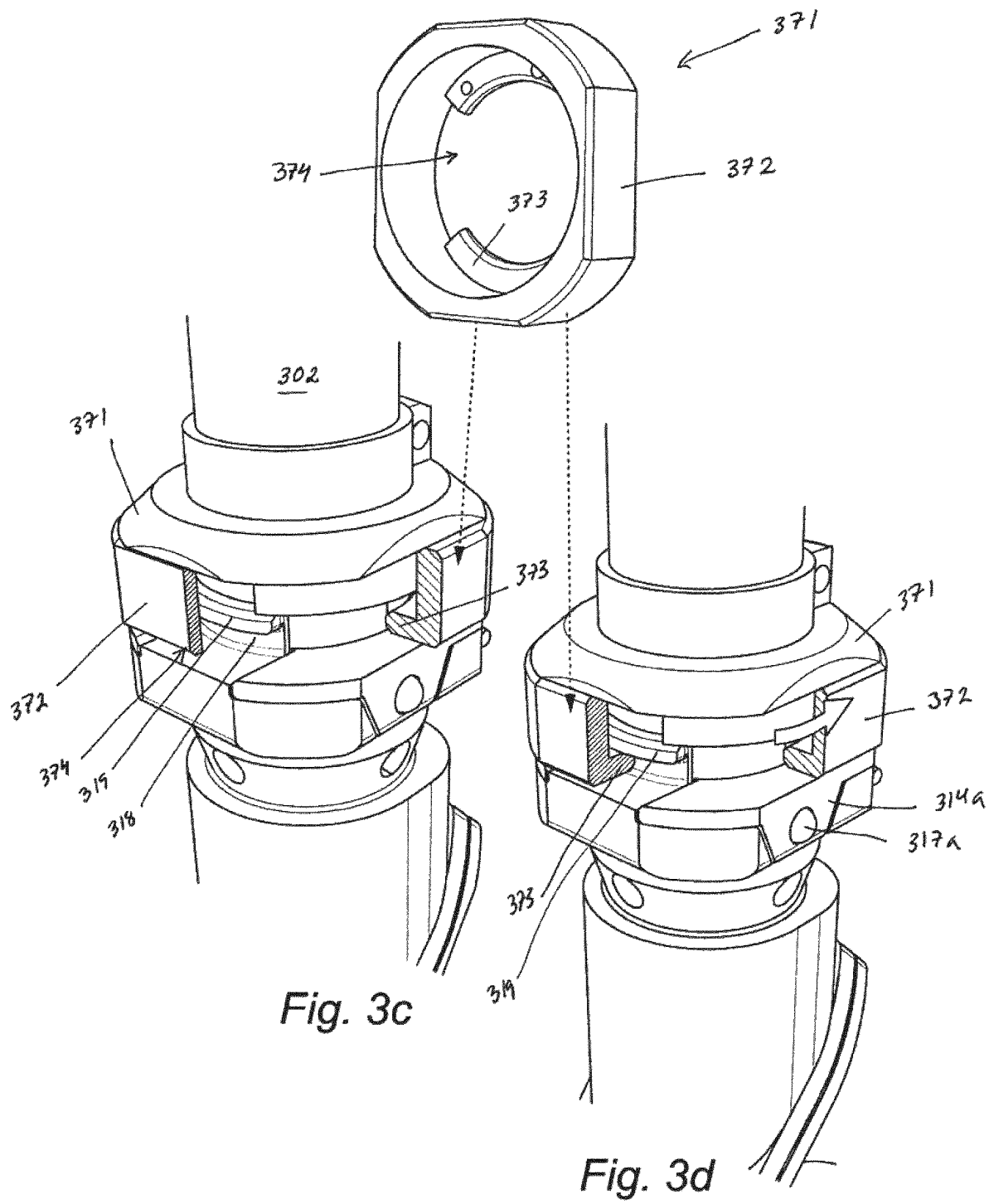

The second locking arrangement is a rotation coupling configured as a rotational locking ring, i.e. the second locking arrangement 371, encircling the second coupling part 360 (see FIGS. 3c and 3d). The rotational locking ring has a peripheral skirt 372 provided with an inwardly folded edge 373 that will engage or disengage a flange 319 provided on the locking protrusion, i.e. the first locking arrangement 318, of the first coupling part 310. When the first locking arrangement has been transferred into a locked configuration the locking protrusion (i.e. the first locking arrangement 318) arranged on the first coupling part 310 has entered the aperture 367 provided in the first end 361 (the mating surface) of the second coupling part 360. The inwardly folded edge 373 of the peripheral skirt 372 is provided with a notch 374 which in an unlocked configuration is aligned with the aperture 367 provided in the second coupling part 360 (see FIG. 3c). The notch 374 on the inwardly folded edge 373 of the peripheral skirt 372 will permit the locking protrusion 318 with the flange 319 to enter the aperture 367.

In order to transfer the second locking arrangement into a locked configuration the locking ring, i.e. the second locking arrangement 371, is rotated in a first direction to a position where the notch 374 is no longer aligned with the aperture 367 (see arrow in FIG. 3d).

When the locking ring is rotated the inwardly folded edge 373 of the peripheral skirt 372 will engage the flange 319 of the locking protrusion (the first locking arrangement 318) and firmly retain the locking protrusion (the first locking arrangement 318) of the first coupling part 310 inside the aperture 367. The second locking arrangement is thereby transferred into the locked configuration. After the second locking arrangement has been locked there is no longer any mobility between the first and second coupling parts 310, 360 and the prosthetic coupling device 300 has been transferred from its intermediate locking state to its connected state.

To disconnect the prosthetic coupling device 300 the rotational locking ring, i.e. the second locking arrangement 371, is rotated in a second direction opposite to the first direction to align the notch 374 arranged on the inwardly folded edge 373 with the aperture 367 on the second coupling part 360. When the notch 374 is aligned with the aperture 367, the flange 319 of the locking protrusion, i.e. the first locking arrangement 318, is disengaged from the inwardly folded edge 373 and the prosthetic coupling device 300 enters the intermediate locking stage where a slight mobility between the coupling parts 310, 360 appears (see FIG. 3c).

Thereafter, the spring loaded push-buttons 317a,b are pressed towards the peripheral side walls 314a,b such that they exit the through-holes 369a,b on the lips 370a,b. The mating surfaces (i.e. the first ends 311, 361) of the coupling parts 310, 360 are now disengaged and the two coupling parts 310, 360 are able to pivot relative to each other by means of the hinged connection (316 and 366). The hinged connection (316 and 366) is released by sliding the pin 316 from the knuckle thereby transferring the prosthetic coupling device 300 into a disconnected state.

It should be noted that due to the hinged connection (316 and 366), which serves as a first and second mating guide members, the user cannot misalign the two prosthetic elements 301, 302 during interconnection. The two coupling parts 310, 360 may only be connected in one way. Thus, there is no risk of connecting the prosthetic elements 301, 302 in an incorrect way. Furthermore, the prosthetic coupling device 300 described in FIGS. 3a-d may be handled by the user without any help from a professional prosthetist or assistant as any personalized adjustments or calibrations of the prosthetic adapter elements remain unaffected when connecting and disconnecting the two coupling parts 310, 360. No tools are required.

Figure 4A:
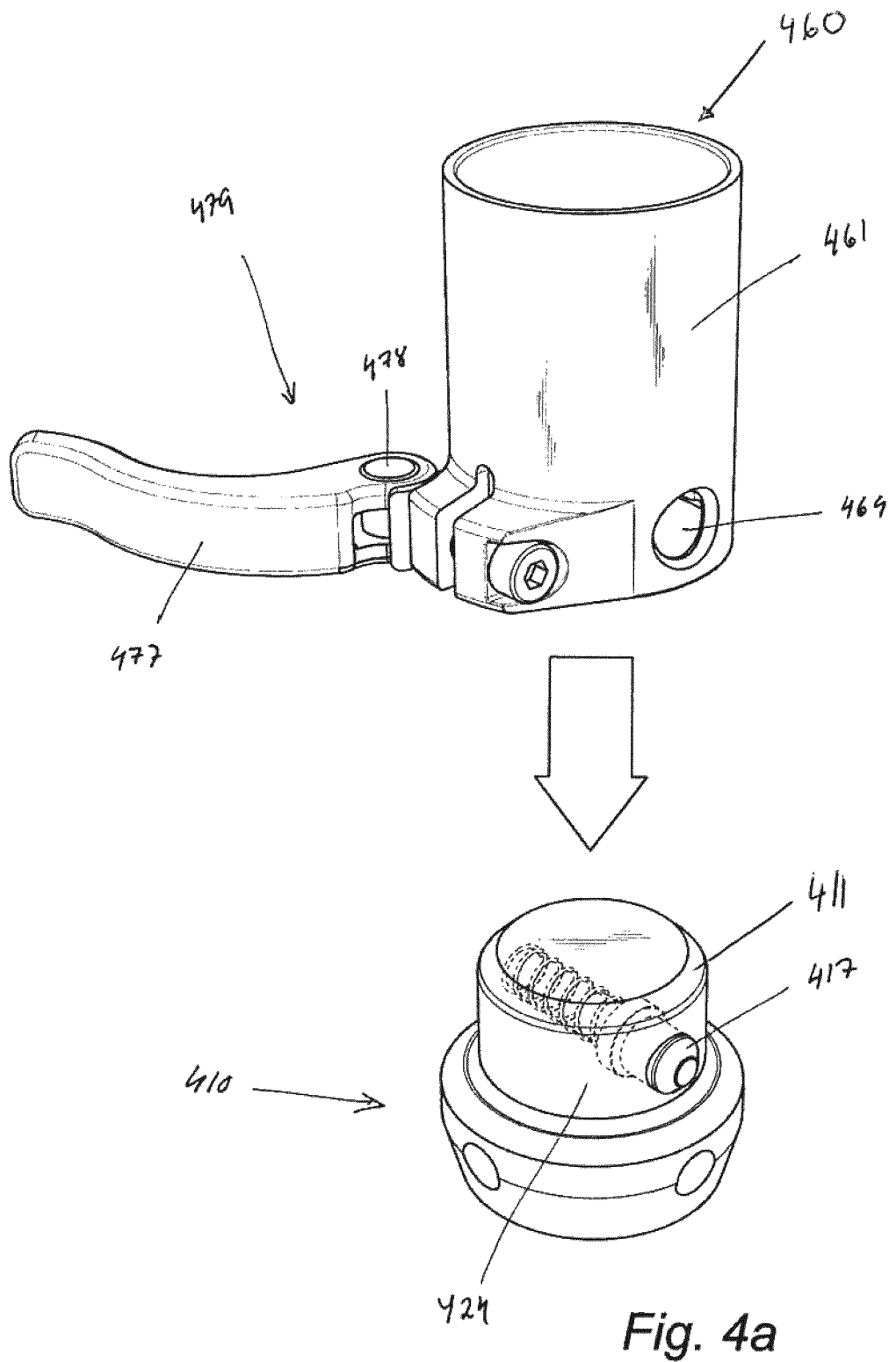
FIGS. 4a-c show a further embodiment of a prosthetic coupling device.
Figure 4B:
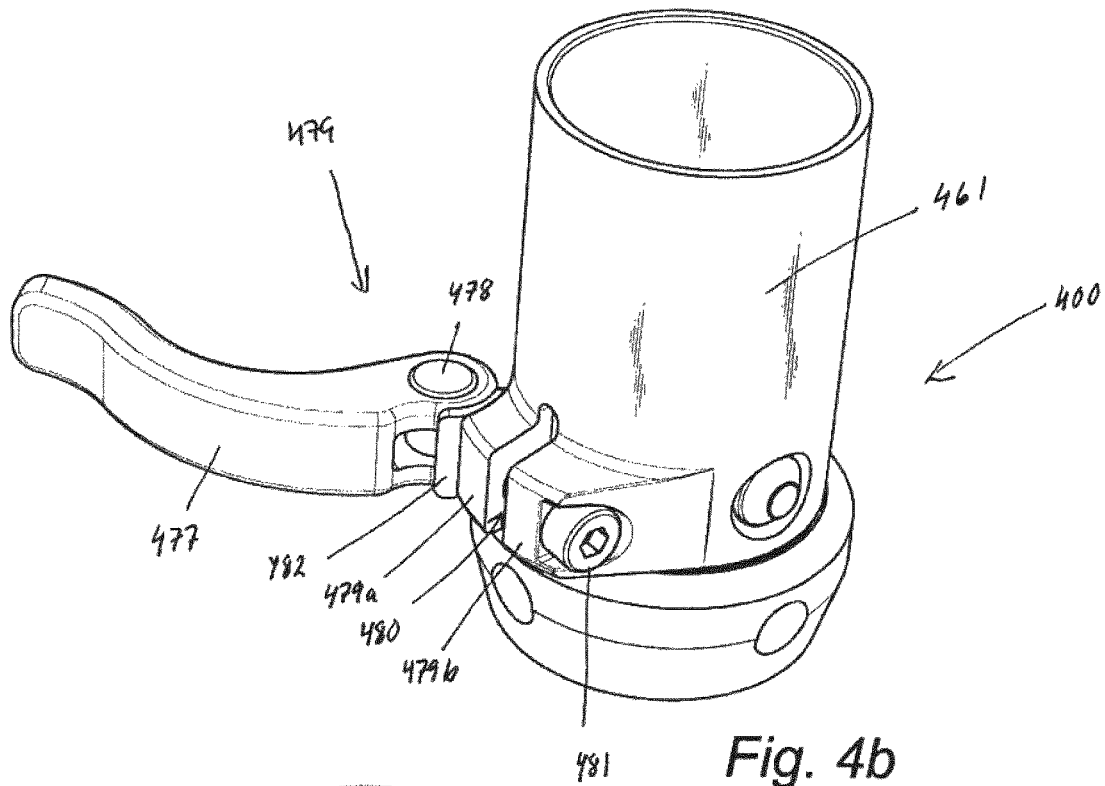
Figure 4C:
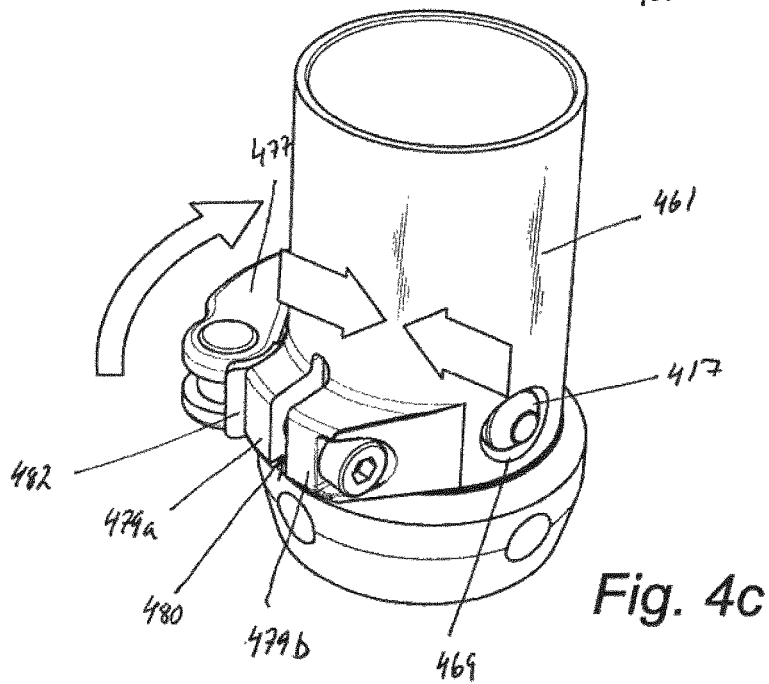

In a further embodiment shown in FIGS. 4a-c the first end 411 of the first coupling part 410 is a first tubular element 411 with an annular circumference that is slightly smaller than a female tubular element that constitutes the first end 461 of the second coupling part 460. The end of the male tubular element will insert in the end of the female tubular element of the second coupling part 460 in a male-female mating configuration (see FIG. 4a).

The male tubular element 411 (i.e. the first end 411 of the first coupling part 410) comprises a spring loaded push button, i.e. the first locking arrangement 417, which protrudes radially outwards from the wall of the male tubular element 411 (i.e. the first end 411 of the first coupling part 410). When the male tubular element is inserted into the female tubular element (i.e. the first end 461 of the second coupling part 460), the spring loaded push button (i.e. the first locking arrangement 417) is pressed towards the wall of the male tubular element and will not spring back until it aligns with a through-hole 469 in the wall of the female tubular element 461. Once the spring loaded push-button protrudes through the through-hole 469 in the wall of the female tubular element, the first and second coupling parts 410, 460 are locked together in a mating configuration (see FIG. 4b).

Due to the alignment of the spring-loaded push button (i.e. the first locking arrangement 417) with the through-hole 469 in the wall of the female tubular element (i.e. first end 461 of a second coupling part 460), the two prosthetic members can be interconnected only in one way. Thus, besides serving as first locking arrangements, the spring-loaded push button and the through-hole 469 in the wall of the female tubular element also serve as mating guide members. This makes it impossible to connect the two members in the "wrong way".

This spring bolt coupling constitutes a first locking arrangement. However, the first locking arrangement does not produce a very tight fit. Although the two prosthetic members will not come apart there will be some slack between the first and second coupling parts 410, 460 which indicates to the user that the prosthetic coupling device 400 has assumed an intermediate locking state and not in its fully connected configuration.

The prosthetic coupling device 400 comprises a second locking arrangement in the shape of a quick release tube clamp (i.e. a second locking arrangement 479) arranged on the second coupling part 460. In FIG. 4b the quick release tube clamp is shown in a released state and in FIG. 4c it is shown in the locked state. The quick release tube clamp has a handle 477 which pivots about a pin 478 and the handle 477 engages a clamp portion of the quick release tube clamp (i.e. the second locking arrangement 479). The clamp portion includes two raised opposing tabs 479a,b and a slot 480 formed in the wall of the female tubular element (i.e. first end 461 of a second coupling part 460) and between the opposing tabs 479a,b of the clamp portion. The clamping portion also has a knurled thumb nut 481.

When the handle 477 is in a released state (see FIG. 4b), the width of the slot 480 between the opposing tabs 479a,b is wide, and when the handle 477 is in a locked state the width of the slot 480 between the opposing tabs 479a,b decreases. The slot 480 formed in the wall of the female tubular element between the opposing tabs 479a,b acts as a spring such that when the handle 477 is moved into the locked state, a cam 482 acts against the spring and narrows the width of the slot 480 such that diameter of the female tubular element decreases and clamps the wall of the male tubular element (i.e. the first end 411 of a first coupling part 410) in a firm grip. When both the first and second locking arrangements (i.e. the spring-loaded push button, i.e. the first locking arrangement 417, and the quick release tube clamp, i.e. the second locking arrangement 479) are in the locked state, there is no longer any slack between the first and second coupling parts 411, 461 and the prosthetic coupling device 400 has been transferred from the intermediate locking state to the connected state.

When the handle 477 is moved into the release position the cam 482 releases its pressure and the slot 480 returns to its release width and although the first and second coupling parts 410, 460 still are connected in the intermediate locking state due to the first locking arrangement, there is a slack between the two coupling parts 411, 461 which makes the user aware that the prosthetic coupling device is not in its fully connected state.

To disconnect the prosthetic coupling device 400 completely, the user has to press the spring loaded push button, i.e. a first locking arrangement 417, through the through-hole 469 in the wall of the female tubular element (i.e. first end 461 of a second coupling part 460) such that the tubular sections of the first and second coupling parts 410, 460 can be pulled apart.

In a slightly different embodiment of the prosthetic coupling device 500 described above the first coupling part 510 comprises a female tubular element (i.e. the first end 511 of the first coupling part 510) fitted with a quick coupling tube clamp 526 on the outer tubular wall 527 (see FIGS. 5a-d). An annular and expandable ring 528 is arranged inside the female tubular element 511 (see FIGS. 5a and 5d). The annular expandable ring 528 has a diameter that is slightly smaller than the diameter of the female tubular element (i.e. the first end 511 of the first coupling part 510) such that a gap 529 is formed between the inner wall 530 of the female tubular element and the outer wall 531 of the annular expandable ring 528. The second coupling part 560 is provided with a male tubular element (i.e. first end 561 of a second coupling part 560) having a diameter such that the male tubular element will insert between the walls 530, 531 of the female tubular element (i.e. the first end 511 of the first coupling part 510) and the annular and expandable ring 528.

Figure 5A:
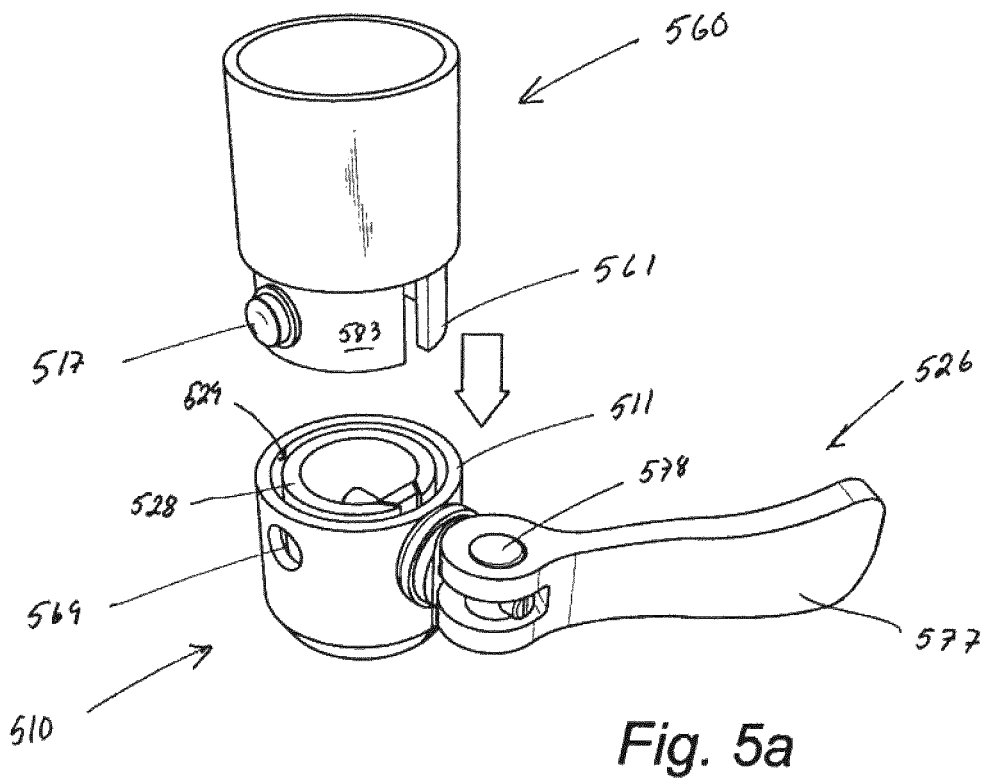
FIGS. 5a-c show a further embodiment of a prosthetic coupling device.
Figure 5B:
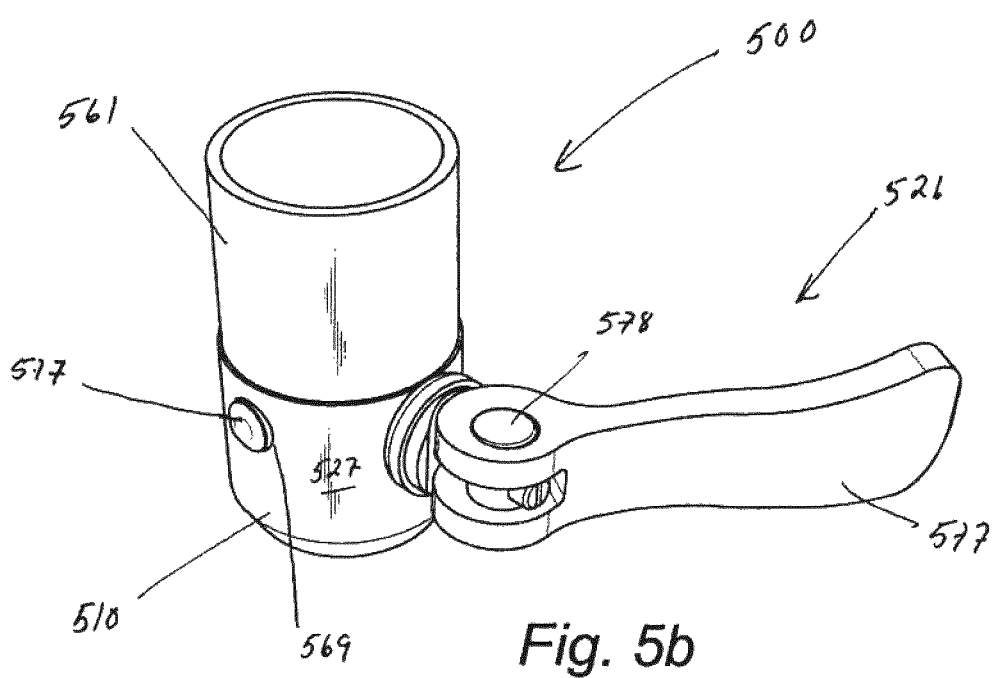
Figures 5C, 5D:
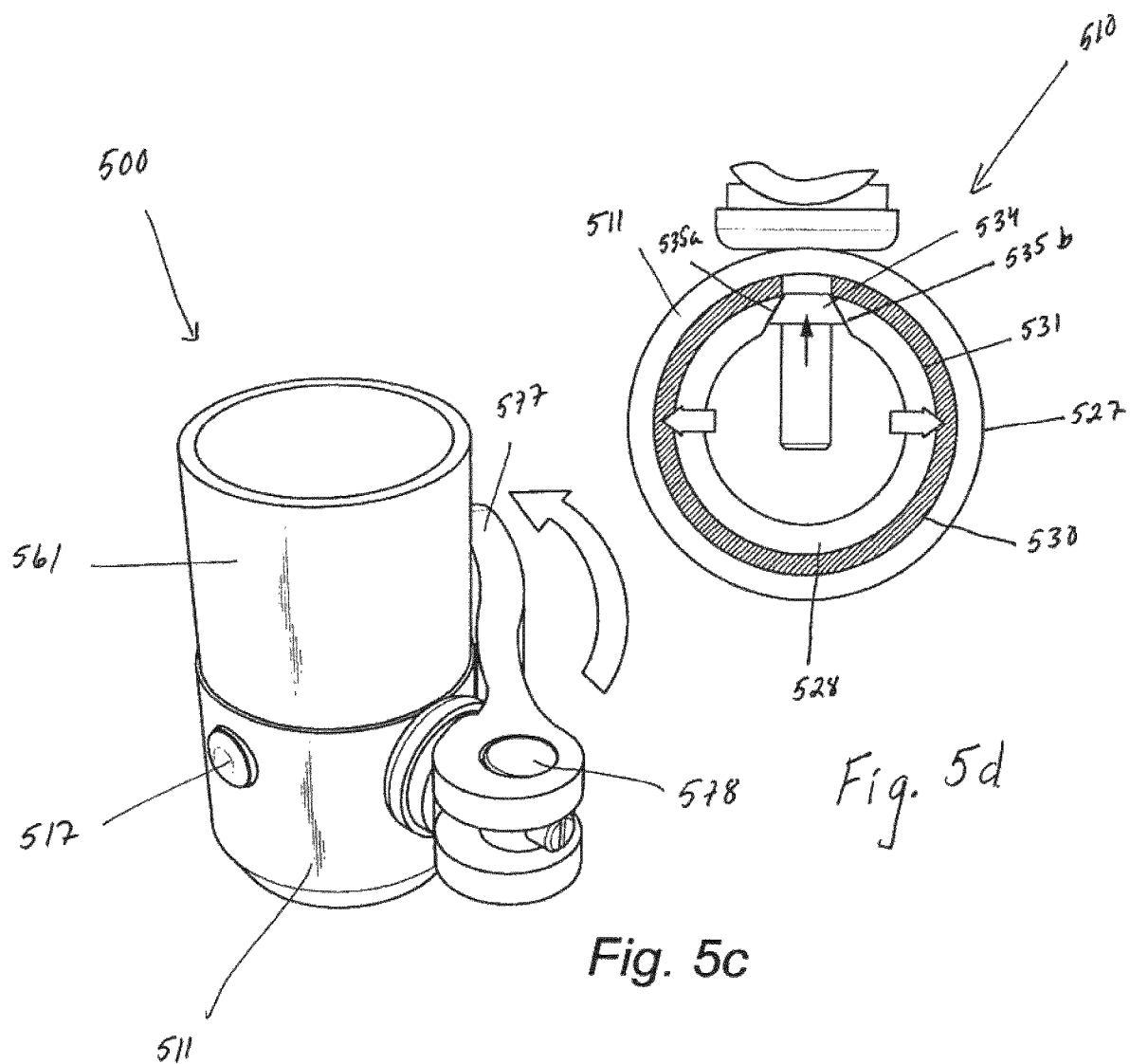

The male tubular element (i.e. first end 561 of a second coupling part 560) is further fitted with a spring loaded push-button, i.e. a first locking arrangement 517, which protrudes radially outwards from the wall 583 of the male tubular element (see FIG. 5a). When the male tubular element is inserted into the gap 529 between the walls 530, 531 of the female tubular element (i.e. the first end 511 of the first coupling part 510) and the annular expandable ring 528, the spring loaded push button, i.e. the first locking arrangement 517, is compressed towards the wall 583 of the male tubular element and will not spring back until it aligns with a through-hole 569 in the wall of the female tubular element. Once the spring loaded push-button protrudes through the through-hole 569 in the wall of the female tubular element, the first and second coupling parts 510, 560 are locked together in a mating configuration (see FIG. 5b). Due to the spring-loaded push button, i.e. the first locking arrangement 517, the two prosthetic members can be interconnected only in one way. The spring-loaded push button and the through-hole 569 in the wall of the female tubular element serve as mating guide members. This makes it impossible to connect the two prosthetic members in the "wrong way".

This spring-loaded push button, i.e. the first locking arrangement 517, constitutes a first locking arrangement. However, the first locking arrangement does not produce a very tight fit. Although the two prosthetic members will not come apart there will be some slack between the first and second coupling parts 510, 560 which indicates to the user that the second locking arrangement is in an intermediate locking state and not in its fully connected configuration.

The prosthetic coupling device 500 comprises a second locking arrangement in the shape of the quick release tube clamp 526 arranged on the first coupling part 510. The quick release tube clamp 526 has a handle 577 which pivots about a pin 578 and engages a clamp portion in the shape of a wedged pin 534 arranged through the wall of the female tubular element (i.e. the first end 511 of the first coupling part 510) and connects to first and second ends 535a,b of the annular expandable ring 528.

When the handle 577 is turned from a release state to a locked state (see FIG. 5c), the wedged pin 534 connected to the two ends 535a, b of the annular expandable ring 528 is pulled radially outwards towards the inner wall 530 of the female tubular element (i.e. the first end 511 of the first coupling part 510) thereby expanding the diameter of the annular expandable ring 528 and clamping the wall 583 of the male tubular element (i.e. the first end 561 of the second coupling part 560) between the walls 530, 531 of the female tubular element and the annular expandable ring 528.

When both the first and second locking arrangements (i.e. the spring-loaded push button (i.e. the first locking arrangement 517) and the quick release tube clamp 526) are in the locked state, there is no longer any slack between the first and second coupling parts 510, 560 and the prosthetic coupling device 500 has been transferred from the intermediate locking state to the connected state.

When the handle 577 is moved into the release position the wedge pin 534 releases its pressure on the two ends 535a, b of the annular expandable ring 528 thereby releasing the firm grip of the male tubular element, i.e. first end 561 of the second coupling part 560. Although the first and second coupling parts 510, 560 still are connected in the intermediate locking state due to the first locking arrangement, there is a slack between the two coupling parts which makes the user aware that the prosthetic coupling device 500 is not in its fully connected state.

To disconnect the prosthetic coupling device 500 completely, the user has to press the spring loaded push-button (i.e. the first locking arrangement 517) through the through-hole 569 in the wall of the female tubular element (i.e. the first end 511 of the first coupling part 510) such that the tubular sections, i.e. first ends 511, 561 of the first and second coupling parts 510, 560 can be pulled apart.

Due to the alignment of the spring-loaded push button (i.e. the first locking arrangement 517) with the through-hole 569 in the wall of the female tubular element (i.e. the first end 511 of the first coupling part 510), the two prosthetic members can be interconnected only in one way. This makes it impossible to connect the two members in the "wrong way".

Figure 6A:
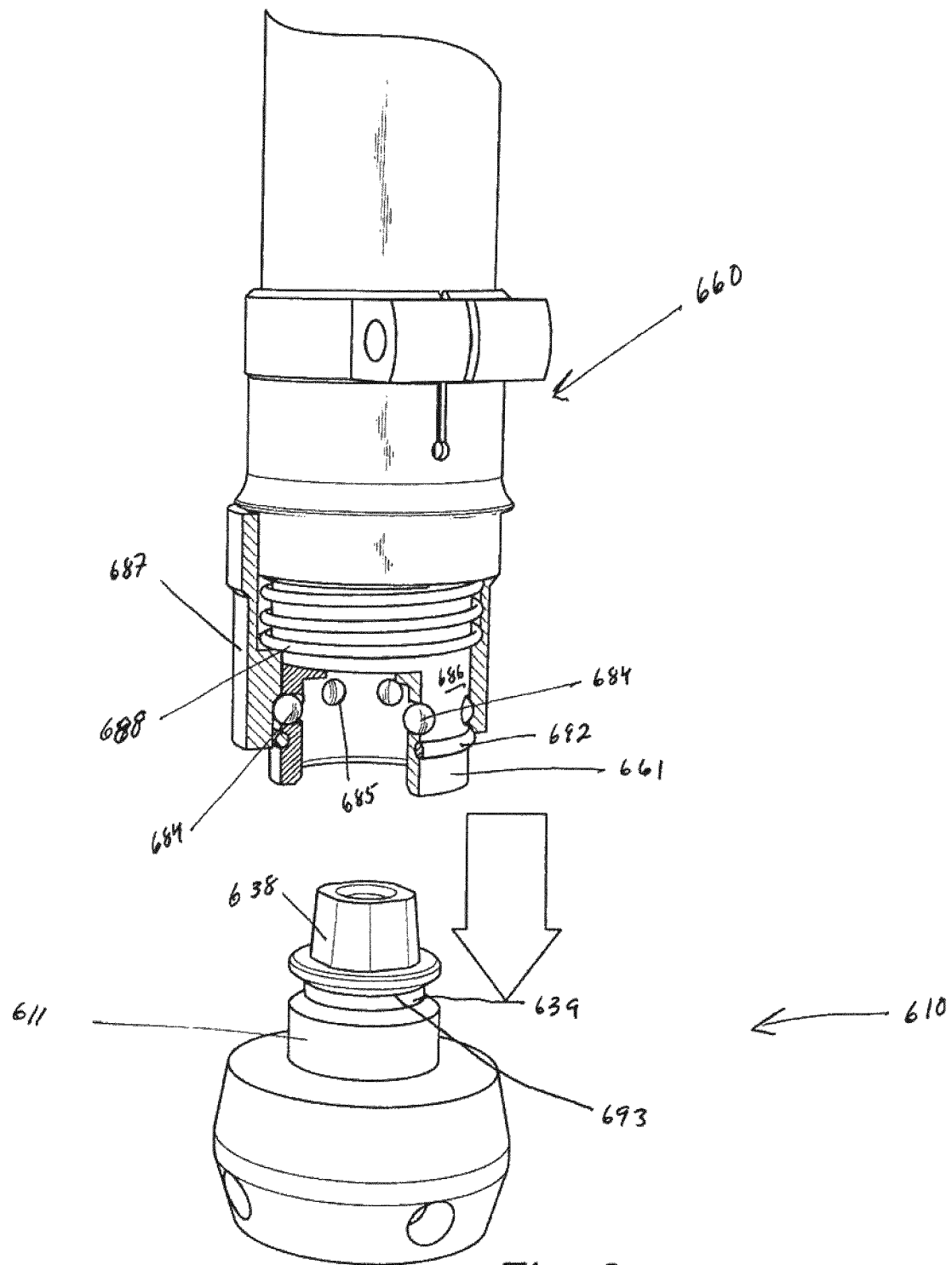
FIGS. 6a-c show a further embodiment of a prosthetic coupling device.
Figures 6B, 6C:
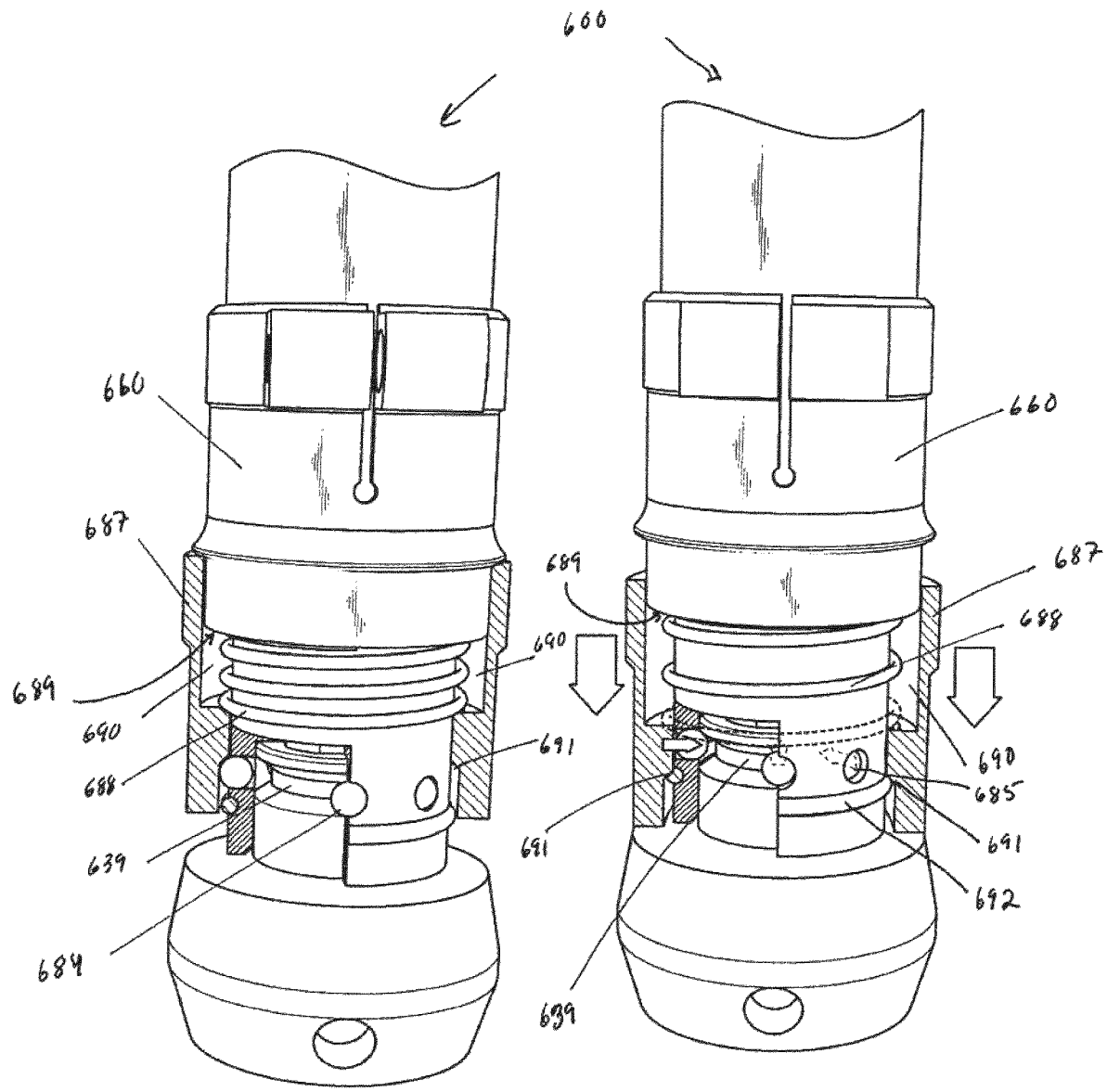
Figure 7A:
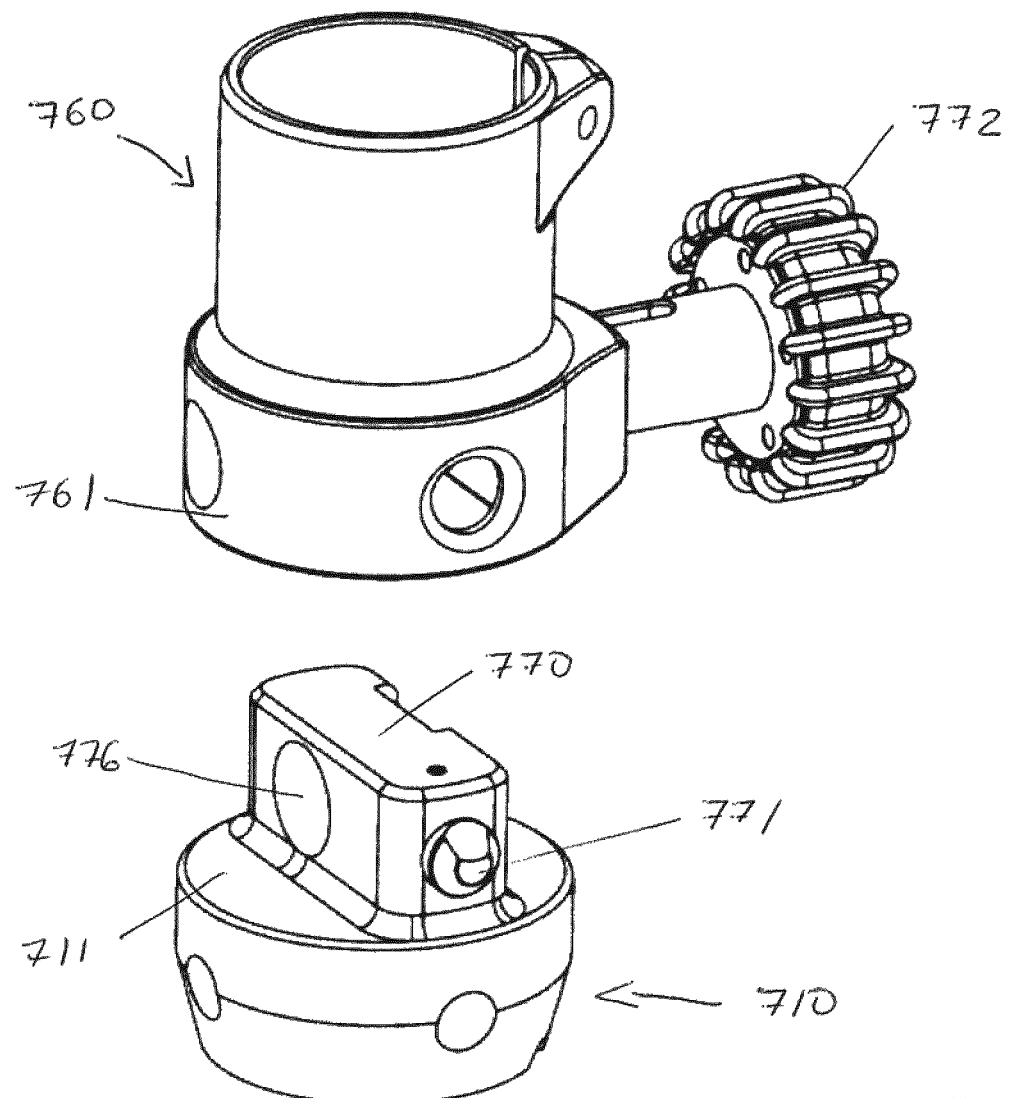
FIGS. 7a-e show a further embodiment of a prosthetic coupling device.
Figure 7B:
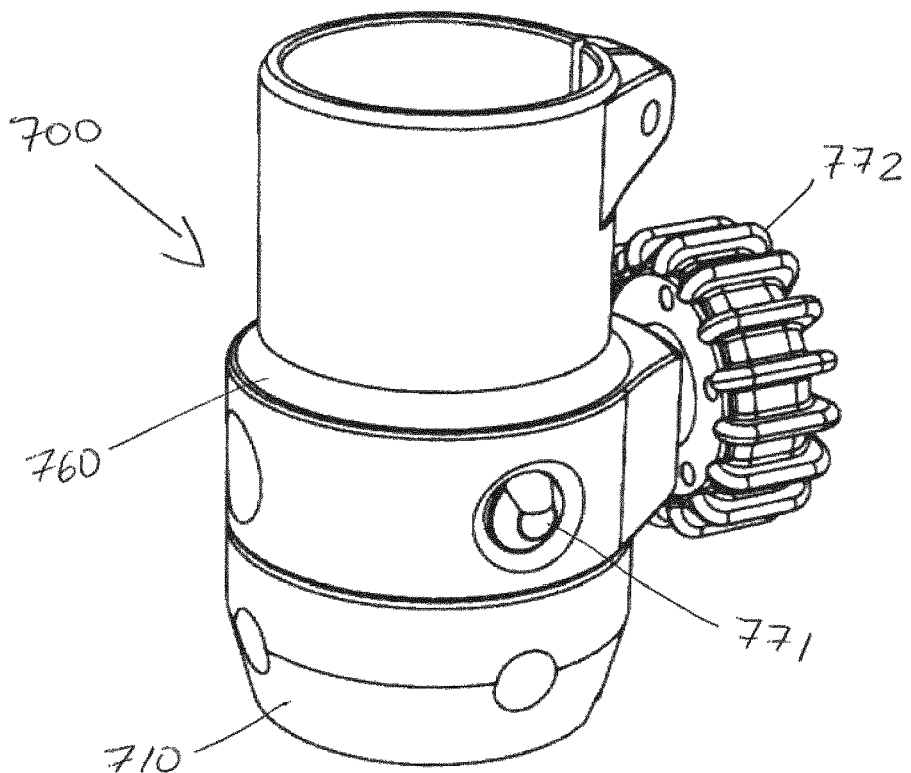
Figure 7C:
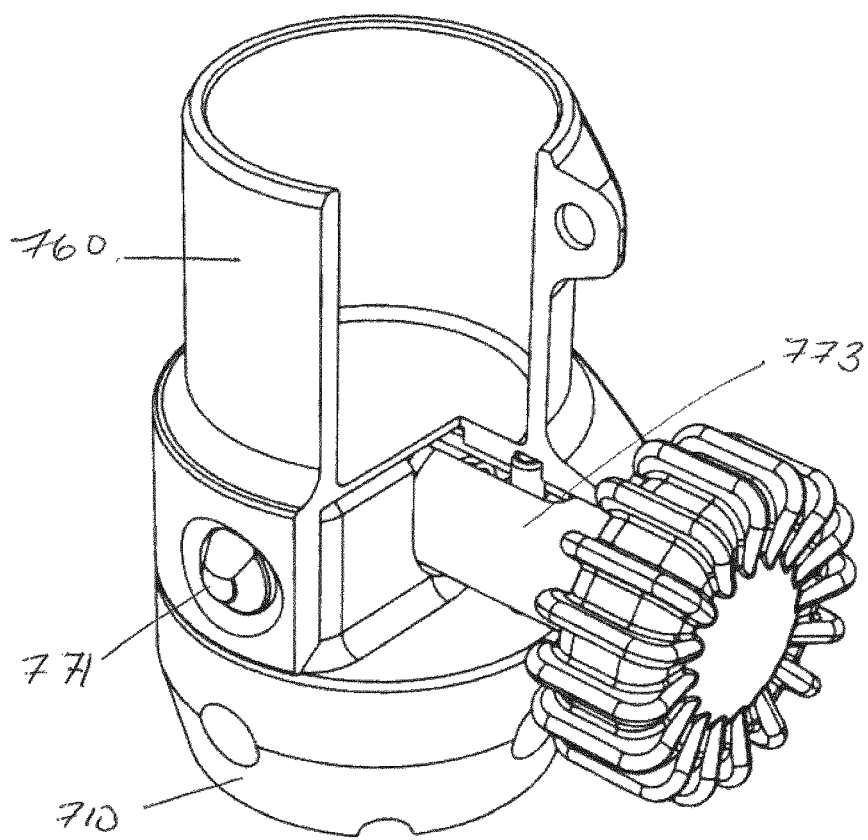
Figure 7D:
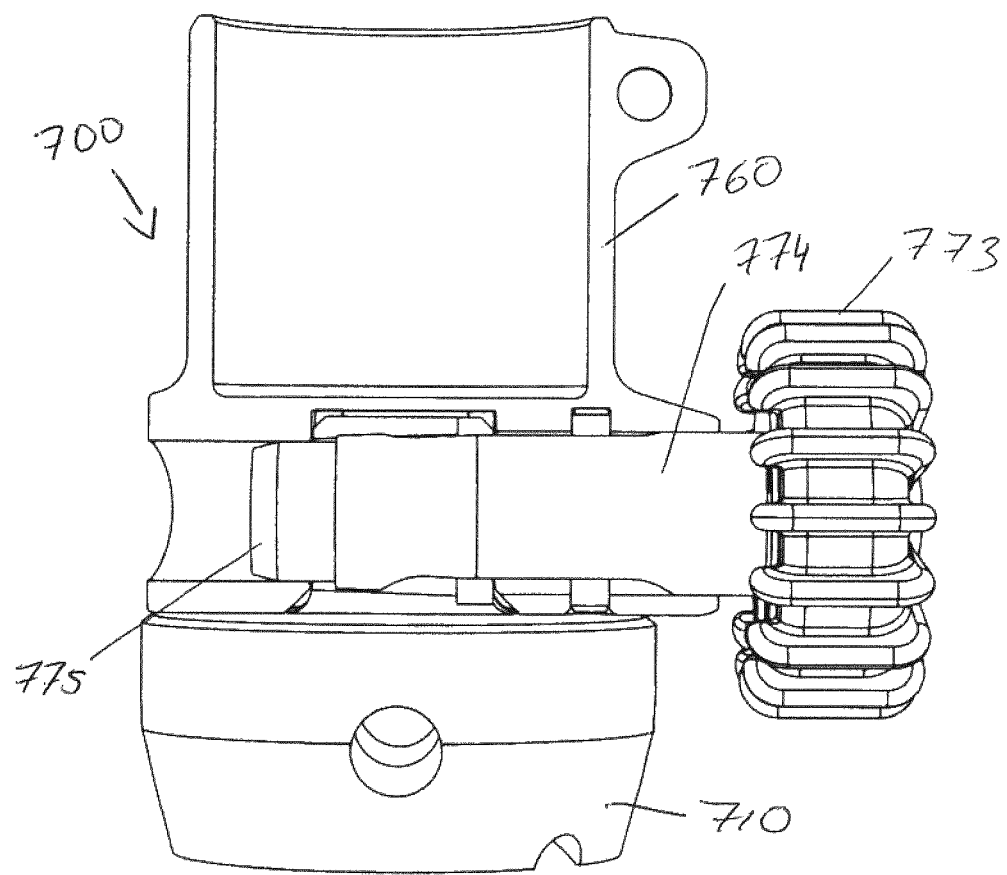
Figure 7E:
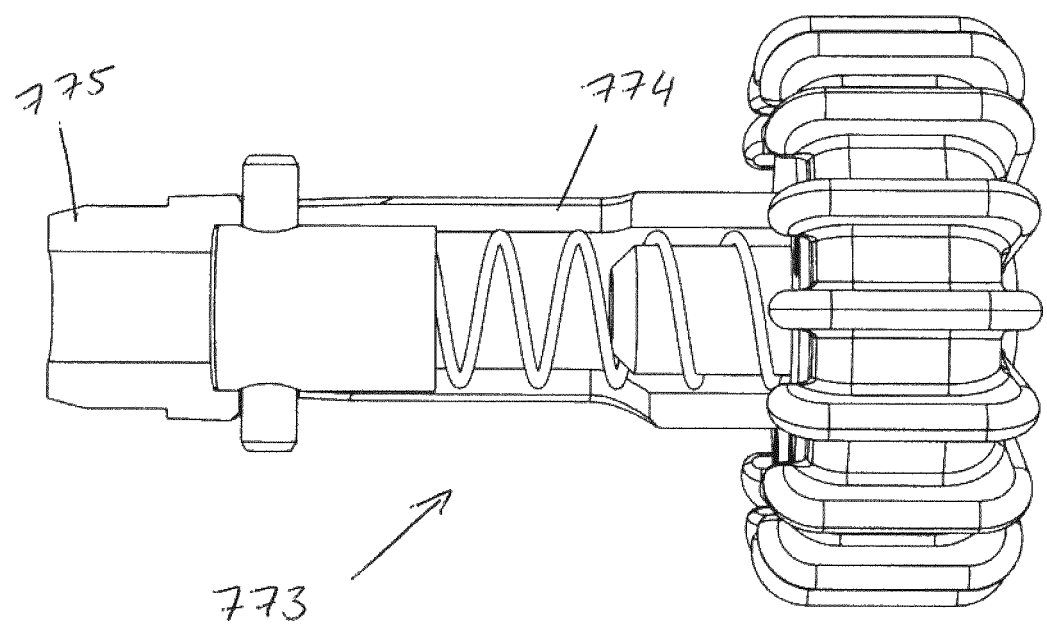

FIGS. 6a-c disclose a further embodiment of a prosthetic coupling device 600 to interconnect prosthetic elements of a prosthetic limb. In this embodiment the first end 611 of the first coupling part 610 constitutes a splined shaft configured to be inserted into a socket arranged on the first end 661 of the second coupling part 660. The splined shaft has a chamfered surface 638 at its distal end and is configured to push detent balls (i.e. a first locking arrangement 684) located in apertures 685 arranged around the wall 686 of the socket outwardly by a cam action of the chamfered portion 638 on the splined shaft. A sliding collar, i.e. a second locking arrangement 687) arranged around the peripheral wall 686 of the socket arranged on the first end 661 of the second coupling part 660 is pushed against a force of a compression coil spring 688. A first end of the coil spring 688 is seated on a circular flat surface 689 arranged on the second coupling part 660 and the other end is seated in a circular recess 690 formed in the sliding collar (i.e. the second locking arrangement 687). The inner wall of the sliding collar is provided with a tapered surface 691 onto which the detent balls (i.e. a first locking arrangement 684) may abut, thereby facilitating the sliding action of the sliding collar into position.

The compression coil spring 688 inherently urges the sliding collar (i.e. the second locking arrangement 687) towards the first coupling part 610 and an inner tapered surface 691 of the slide collar urges the detent balls (i.e. a first locking arrangement 684) inwardly into the apertures 685 owing to a wedge action of the tapered surface 691 (see FIGS. 6b and 6c). When the splined shaft (i.e. the first end 611 of a first coupling part 610) arrives in position, the detent balls are forced into a ball receiving groove (i.e. a first locking arrangement 639) in the splined shaft by the action of the inner tapered surface 691 of the sliding collar (i.e. the second locking arrangement 687). The first locking arrangement 684 (i.e. the detent balls) has been transferred to a locked configuration. However, although connected together, there is still some mobility between the first and second coupling parts in this intermediate locking state.

The mobility between the first and second coupling parts 610, 660 will not cease until also the second locking arrangements have been transferred to the connected configuration. To reach this configuration the sliding collar, i.e. the second locking arrangement 687, is moved towards the first end 611 of the first coupling part 610 by the action of the compression coil spring 688. The movement of the sliding collar will continue until the tapered surface 691 of the sliding collar abuts against a stopping flange 692 arranged on the peripheral wall 686 of the first end 661 of the second coupling part 660. In this position the sliding collar, i.e. the second locking arrangement 687, is continuously urged against the stopping flange 692 by the compression coil spring 688 and will thereby be unable to release the detent balls (i.e. a first locking arrangement 684) from the ball receiving groove (i.e. a first locking arrangement 639) in the splined shaft (i.e. the first end 611 of a first coupling part 610), thereby preventing the splined shaft from disconnecting the socket arranged on the first end 661 of the second coupling part 660. The prosthetic coupling device 600 has now entered the connected state.

A notch is provided at the first end 661 of the second coupling part 660 into which a protrusion located in the splined shaft (i.e. the first end 611 of a first coupling part 610) fits. The notch and the protrusion will together serve as mating guide members to ensure that the first and second coupling parts 610, 660 are properly aligned before being connected.

In order to remove the splined shaft (i.e. the first end 611 of the first coupling part 610) from the socket (i.e. first end 661 of the second coupling part 660), the sliding collar (i.e. the second locking arrangement 687) is moved by the operator against the force of the compression coil spring 688 towards the second coupling part 660. The second locking arrangement is now transferred into the release configuration. As the sliding collar is pushed towards the second coupling part 660, it arrives at the position where the detent balls (i.e. a first locking arrangement 684) are urged outwardly by an action of a concaved edge 693 (see FIG. 6a) of the ball receiving groove (i.e. the first locking arrangement 639) on the splined shaft. The splined shaft may now be removed from the first end 661 of the second coupling part 660. Also the first locking arrangement has been transferred to the release position and the prosthetic coupling device 600 has been disconnected.

FIGS. 7a-e disclose a further embodiment of a prosthetic coupling device 700 to interconnect prosthetic elements of a prosthetic limb. In this embodiment, the first end 711 of the first coupling part 710 constitutes a protrusion 770 in the form of a trapezium. The protrusion 770 is configured to be inserted into a corresponding recess arranged on the first end 761 of the second coupling part 760 of the coupling device 700. Thus, the first and second coupling parts 710, 760 each have first ends 711, 761 comprising surfaces that will fit together in a mating configuration and which are connectable to one another by means of a spring loaded push-button (i.e. the first locking arrangement 771). The spring loaded push-button corresponds to the spring-loaded push button described above, e.g. for FIG. 3a-d. The second locking mechanism 772 constitutes a screw 773 having a shaft 774 with a conical end 775 configured to be inserted into a conical through-hole 776 in the first end 711 of the first coupling part 710 and into a through-hole in the first end 761 of the second coupling part 760. The conical through-hole 776 in the first end 711 of the first coupling part 710 is arranged in the protrusion 770. When the two parts 710, 760 are assembled the two through-holes are not aligned on the same axis. When the screw 773 is screwed, the shaft 774 will be displaced, pressing its conical end 776 in to the through-holes, and since its conical configuration, the conical end 775 will exert a force on the inside walls of the through-holes, thereby forcing the two coupling parts 710, 760 together. The protrusion 770, when inserted into the second coupling part 760, prevents rotation of the second coupling part 760 relative to the first coupling part 710, thereby providing a third locking arrangement which is a rotation locking arrangement.

In the embodiments disclosed in FIGS. 4, 5, 6, and 7 the second ends of the first and second coupling parts are of course connectable to a first and second prosthetic adapter element respectively although not explicitly shown in all figures. The types of adapter connections required at the second ends depend of course on the kind of prosthetic elements to be interconnected by the coupling device. For example when a prosthetic foot is connected to a lower end of a lower leg the second end of the first coupling part is advantageously fitted with an annular socket portion with four set-screws disposed therearound which has been aligned to a pyramidal boss of a male adapter element in a conventional manner. The second end of the second coupling element may in such an embodiment be provided with a female tube clamp to connect to a pylon of a lower leg.

The above mentioned and described embodiments are only given as examples and should not be limiting to the present invention. Other solutions, uses, objectives, and functions within the scope of the invention as claimed in the below described patent claims should be apparent for the person skilled in the art.

REFERENCE SIGNS 100, 200, 300, 400, 500, 600, 700 prosthetic coupling device
101, 201 first prosthetic member 213 prosthetic adapter element of a first prosthetic member
102, 202 second prosthetic member
263 prosthetic adapter element on a second prosthetic member
210, 310, 410, 510, 610, 710 first coupling part
314a, 314b peripheral side walls of the first coupling part
319 flange
211, 311, 411, 511, 611, 711 first end of a first coupling part
212, 312 second end of a first coupling part
260, 360, 460, 560, 660, 760 second coupling part
261, 361, 461, 561, 661, 761 first end of a second coupling part
318, 366, 317, 417, 517, 684, 639, 771 first locking arrangement
371, 479, 687, 772 second locking arrangement
314a, 314b peripheral side walls of the first coupling part
316, 478, 578 pin
317a, 317b push-button
367 aperture arranged in the first end of a second coupling part
369a, 369b, 469 through-hole
370a, 370b lips
372 peripheral skirt
373 inwardly folded edge
374 notch
530, 531, 583, 686 wall
477, 577 handle
479a, 479b tabs
480 slot
481 knurled thumb nut
482 cam
526 quick release tube clamp
527 outer tubular wall
528 expandable ring
529 gap
534 wedged pin
535a, 535b end of the annular expandable ring 528
638 chamfered surface
685 aperture
688 coil spring
689 circular flat surface
690 recess
691 tapered surface
692 stopping flange
693 concaved edge
770 protrusion
773 screw
774 shaft
775 conical end
776 through-hole

The invention claimed is:

1. A prosthetic coupling device comprising a first coupling part and a second coupling part, said first coupling part comprising a first end and a second end and said second coupling part comprising a first end and a second end, said first end of said first coupling part being connectable to said first end of said second coupling part, said second end of said first coupling part being configured to connect to a prosthetic adapter element of a first prosthetic member for a foot or a leg, and said second end of said second coupling part being configured to connect to a prosthetic adapter element on a second prosthetic member for the foot or the leg;
wherein said prosthetic coupling device comprises first and second manually operable locking arrangements being separately operable and each having a locked configuration and a release configuration, said coupling device being transferable from a connected state to a disconnected state only when both said locking arrangements are in said release configuration, and
wherein each of the first and second manually operable locking arrangements is configured to lock the first coupling part and the second coupling part in an axial direction.

2. The prosthetic coupling device according to claim 1, wherein the prosthetic adapter element of said first or second prosthetic members is selected from the group consisting of 4-hole Linking plates, 4-hole male pyramids, 4-hole female pyramids, 4-hole pyramid receiver adapters, female double adapter, male double adapter, male-female double adapter, Sach foot adapter, female pylons, male adapters, female adapters, male tube clamps, female tube clamps, and/or 4-hole tube clamps.

3. The prosthetic coupling device according to claim 1, wherein the first and second locking arrangements are independently selected from slide-in couplings, clamp couplings, spring bolt couplings, snap-fit couplings, and rotatable couplings.

4. The prosthetic coupling device according to claim 1, wherein said first locking arrangement is a spring loaded push-button.

5. The prosthetic coupling device according to claim 1, wherein said second locking arrangement is a screw having a shaft with a conical end.

6. The prosthetic coupling device according to claim 1, wherein said first locking arrangement is a spring loaded push-button and said second locking arrangement is a screw having a shaft with a conical end.

7. The prosthetic coupling device according to claim 1, wherein an intermediate locking state of the prosthetic coupling device is assumed between the connected state and the disconnected state.

8. The prosthetic coupling device according to claim 7, wherein there is a mobility between said first and second coupling parts when said prosthetic coupling device has assumed an intermediate locking state.

9. The prosthetic coupling device according to claim 1, wherein said first and second locking arrangements of said first ends of said first and second coupling parts comprise mating guide members.

10. Use of a coupling device according to claim 1.

11. A prosthetic assembly configured to be attached to a prosthetic socket or to an osseointegrated coupling, wherein the assembly comprises two prosthetic members interconnected by a coupling device according to claim 1.

12. A method for connecting and disconnecting a first a prosthetic member to a second prosthetic member; wherein
a first locking arrangement of the prosthetic coupling device according to claim 1, is transferred from a release configuration to a locked configuration, whereby said prosthetic coupling device assumes an intermediate locking state; and
a second locking arrangement of the prosthetic coupling device is transferred from a release configuration to a locked configuration, whereby said prosthetic coupling device is transferred from a disconnected state to a connected state; and thereafter
said second locking arrangement is transferred from a locked configuration to a release configuration, whereby said prosthetic coupling device assumes an intermediate locking state; and
said first locking arrangement is transferred from a locked configuration to a release configuration, whereby said prosthetic coupling device is transferred from a connected state to a disconnected state.

13. A method for connecting a first a prosthetic member to a second prosthetic member, wherein:
- a first locking arrangement of the prosthetic coupling device according to claim 1, is transferred from a release configuration to a locked configuration, whereby said prosthetic coupling device assumes an intermediate locking state; and
- a second locking arrangement of the prosthetic coupling device is transferred from a release configuration to a locked configuration, whereby said prosthetic coupling device is transferred from a disconnected state to a connected state.

14. A method for disconnecting a first a prosthetic member from a second prosthetic member, wherein
- a second locking arrangement of the prosthetic coupling device according to claim 1, is transferred from a locked configuration to a release configuration, whereby said prosthetic coupling device assumes an intermediate locking state; and
- said first locking arrangement is transferred from a locked configuration to a release configuration, whereby said prosthetic coupling device is transferred from a connected state to a disconnected state.

15. The prosthetic coupling device according to claim 1 further comprising a third locking arrangement, wherein the third locking arrangement is a rotational locking arrangement.

* * * * *